United States Patent [19]
Kauvar et al.

[11] Patent Number: 5,955,432
[45] Date of Patent: *Sep. 21, 1999

[54] METABOLIC EFFECTS OF CERTAIN GLUTATHIONE ANALOGS

[75] Inventors: Lawrence M. Kauvar, San Francisco; Amy S. Morgan, Oakland; Matthew H. Lyttle, Point Reyes Station, all of Calif.; Richard F. Borch, Pittsford, N.Y.

[73] Assignee: Terrapin Technologies, Inc., S. San Francisco, Calif.

[*] Notice: This patent is subject to a terminal disclaimer.

[21] Appl. No.: 08/675,095

[22] Filed: Jul. 3, 1996

Related U.S. Application Data

[63] Continuation-in-part of application No. 08/636,516, Apr. 19, 1996, abandoned, which is a continuation-in-part of application No. 08/482,645, Jun. 7, 1995, which is a continuation-in-part of application No. 08/305,993, Sep. 19, 1994, which is a continuation-in-part of application No. 08/126,229, Sep. 24, 1993, Pat. No. 5,599,903, which is a continuation-in-part of application No. 07/863,564, Apr. 3, 1992, abandoned.

[51] Int. Cl.$^6$ .............................. A61K 38/06; C07K 5/08
[52] U.S. Cl. .............................................. 514/18; 530/331
[58] Field of Search ................................ 514/18; 530/331

[56] References Cited

U.S. PATENT DOCUMENTS

| | | |
|---|---|---|
| 4,851,388 | 7/1989 | Bright . |
| 4,963,263 | 10/1990 | Kauvar . |
| 5,133,866 | 7/1992 | Kauvar . |
| 5,204,241 | 4/1993 | Pero . |
| 5,430,045 | 7/1995 | Goldberg et al. . |

FOREIGN PATENT DOCUMENTS

| | | |
|---|---|---|
| 0 480 061 | 4/1992 | European Pat. Off. . |
| 1 317 275 | 5/1973 | United Kingdom . |
| WO 86/00991 | 2/1986 | WIPO . |
| WO 86/06487 | 11/1986 | WIPO . |
| WO 89/03430 | 4/1989 | WIPO . |
| WO 90/12088 | 10/1990 | WIPO . |
| WO 91/17240 | 11/1991 | WIPO . |
| WO 92/00320 | 1/1992 | WIPO . |
| WO 92/19767 | 11/1992 | WIPO . |
| WO 95/08563 | 3/1995 | WIPO . |

OTHER PUBLICATIONS

Ciaccio, P.J. et al., *Molecular Pharmacology*, vol. 48(4), pp. 639–647 (1995).
Cournoyer, D. et al., Annual Meeting of the Candian Society for Clinical Investigation and the Royal College of Physicians and Surgeons of Canada, Montreal, Quebec, Canada, Sep. 13–17, 1995, *Clinical and Investigative Medicine*, vol. 18(4Suppl.) (1995).
Morgan, S. et al., *Cancer Chemotherapy and Pharmacology*, vol. 37(4), pp. 363–370 (1996).
Adang, et al., "The glutathione–binding site in glutathione S–transferases, Investigation of the cysteinyl, glycyl and γ–glutamyl domains," *Biochem. J.* (1990) 269:47–54.
Camble, et al., "The Use of S–Benzylthiomethyl–L–cysteine in Peptide Synthesis: Synthesis of Glutathione and Homo-glutatione," *J. Chem. Soc.* (1968) 7(1515):1219–1224.
Campling, et al., "Do glutathione and related enzymes play a role in drug resistance in small cell lung cancer cell lines?" *Br. J. Cancer* (1993) 68:327–335.
Castro, et al., "Differences among human tumor cell lines in the expression of glutathione transferases and other glutathione–linked enzymes," *Oxford University Press*, 1569–1576 (1990).
Castro, et al., "Glutathione analogue sorbents selectively bind glutathione S–transferase isoenzymes," *Biochem. J.* (1993) 292:371–377.
Chatterjee, et al., "Idiotypic antibody immunotherapy of cancer," *Cancer Immunol. Immunother.* (1994) 38:75–86.
Dermer, "Another Anniversary for the War on Cancer" *Biotechnology* (1994) 12:320.
Flatgaard, et al., "Isozyme specificity of novel glutathione–S–transferase inhibitors" *Cancer Chemother. Pharmacol.* (1993) 33:63–70.
Held, et al., "Effect of Dimethyl Fumarate on the Radiation Sensitivity of Mammalian Cells in Vitro," *Radiation Research* (1988) 115:495–502.
Kasai, et al., "γ–Glutamyl Peptides of *Vigna Radiata* Seeds," (1986) 25:679–682.
Kauvar, et al. "Paralog Chromatography" *Biotechniques* (1990) 8:204–209.
Kauvar, "Pharmaceutical Targeting of GST Isozymes," *Structure and Function of Glutathione Transferases*, CRC Press, (1993) pp. 257–267.
Lyttle, et al., "Construction of Affinity Sorbents Utilizing Glutathione Analogs," *Peptide Research* (1992) 5(6):336–342.
Lyttle, et al "Glutathione–S– transferase Activates Novel Alkylating Agents" *J. Med. Chem.* (1994) 37:1501–1507.

(List continued on next page.)

*Primary Examiner*—Paula K. Hutzell
*Assistant Examiner*—Benet Prickril
*Attorney, Agent, or Firm*—Morrison & Foerster LLP

[57] ABSTRACT

Compounds of the formula

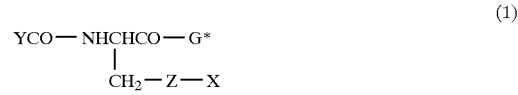

and the esters, amides, amide/esters and salts thereof, wherein YCO is γ-glu or β-asp;

G* is phenylglycine or glycine;

Z is $CH_2$, O or S; and

X is a hydrocarbon radical selected from $C_6$–$C_8$ alkyl or selected aromatic groups are useful in modulating hematopoiesis in bone marrow, mitigating the bone-marrow-destructive effects of a chemotherapeutic agent, and in potentiating the toxicity of chemotherapeutic agents.

38 Claims, 27 Drawing Sheets

OTHER PUBLICATIONS

Mannervik, et al., "Identification of Three Classes of Cytosolic Glutathione Transferase Common to Several Mammalian Species: Correlation Between Structural Data and Enzymatic Properties" *Proc. Natl. Acad. Sci. USA* (1985) 82:7202–7206.

Mannervik, et al., "Glutathione Transferases–Structure and Catalytic" *CRC Crit. Rev. Biochem.* (1988) 23:283–337.

Morris "Synthesis of the α– and γ–Isomers of Glutamylcystinylvaline," *Biochem. J.;* (1960) 76:349.

Mozer, et al., "Purification and Characterization of Corn Glutathione S–Transferase," *Biochemistry* (1983) 22:1068–1072.

O'Dwyer, et al., "Phase I Study of Thiotepa in Combination with the Glutathione Transferase Inhibitor Ethacrynic Acid" *Cancer Res.* (1991) 51:6059–6065.

O'Dwyer, et al., "Depletion of Glutathione in Normal and Malignant Human Cells In Vivo by Buthionine Sulfoximine: Clinical and Biochemical Results" *JNCI* (1992) 84:264–267.

Principato, et al., "Effects of some S–Blocked Glutathione Derivatives on the Prevalent Glyoxalase II (a Form) of Rat Liver," *Enzyme* (1989) 41(3):175–180.

Puchalski, et al., "Expression of Recombinant Glutathione S–Transferase π, Ya, or $Yb_1$ Confers Resistance to Alkylating Agents" *Proc. Natl. Acad. Sci. USA* (1990) 87:2443–2447.

Ricci, et al., "Detection of Glutathione Transferase Activity on Polyacrylamide Gels" *Analytical Biochemsitry* (1984)143:226–230.

Ripple et al. "Characteristics of the Glutathione/Glutathione–S–Transferase Detoxification System in Melphalan Resistant Human Prostate Cancer Cells" *J. Urology* (1993) 150:209–214.

Schisselbauer, et al., "Characterization of Glutathione S–Transferase Expression in Lymphocytes From Chronic Lymphocytic Leukemia Patients" *Cancer Research* (1990) 50:3562–3568.

Sheh, et al., "Synthesis of Cyclic Peptide Homologs of Glutathione as Potential Antitumor Agents" *Int. J. Peptide Protein Res.* (1990) 35:55–62.

Smith, et al. "Denitrosation of 1,3–Bis(2–chloroethyl)–1–nitrosourea by Class Mu Glutathione Transferases and Its Role in Cellular Resistance in Rat Brain Tumor Cells" *Cancer Research* (1989). 49:2621–2625.

Takeo, et al., "Binding Constants of Dextrans and Isomaltose Oligosaccharides to Dextran–Specific Myeloma Proteins Determined by Affinity Electrophoresis" *The Journal of Immunology* (1978) 121:2305–2310.

Tew, et al., "Ethacrynic Acid and Piriprost an Enhancers of Cytotoxicity in Drug Resistant and Sensitive Cell Lines" *Cancer Research* (1988) 48:3622–3625.

Van Bladeren, et al., "The Inhibition of Glutathione S–Transferases: Mechanisms, Toxic Consequences and Therapeutic Benefits" *Pharmac. Ther.* (1991) 51:35–46.

Vos, et al., "Differential Induction of Rat Hepatic Glutathione S–Transferase Isoenzymes by Hexachlorobenzene and Benzyl Isothiocyanate" *Biochemical Pharmacology* (1988) 37(6):1077–1082.

Waxman, "Glutathione S–Transferases: Role in Alkylating Agent Resistance and Possible Target for Modulation Chemotherapy—A Review" *Cancer Research* (1990) 50:6449–6454.

Webster's II New Riverside University Dictionary, The New Riverside Publishing Company, 1988, p. 849.

Wiencke, et al., "Human Glutathione S–Transferase Deficiency as a Market of Susceptibility to Epoxide–Induced Cytogenetic Damage" *Cancer Research* (1990) 50:1585–1590.

- ■ — STERILE WATER
- • — FLUOROURACIL 150mg/kg
- ▲ — FLUOROURACIL+ TER199qd. 120 mg/kg
- ♦ — FLUOROURACIL+ TER199 BID. 60 mg/km

— STERILE WATER

— FLUOROURACIL 150mg/kg

— FLUOROURACIL+ TER199qd. 120 mg/kg

— FLUOROURACIL+ TER199 BID. 60 mg/km

METABOLIC EFFECTS OF CERTAIN GLUTATHIONE ANALOGS

This application is a continuation-in-part of U.S. Ser. No. 08/636,516 filed Apr. 19, 1996, now abandoned which is a continuation-in-part of U.S. Ser. No. 08/482,645 filed Jun. 7, 1995 which is a continuation-in-part of U.S. Ser. No. 08/305,993 filed Sep. 19, 1994 which is a continuation-in-part of Ser. No. 08/126,229 filed Sep. 24, 1993, now U.S. Pat. No. 5,599,903, which is a continuation-in-part of Ser. No. 07/863,564 filed Apr. 3, 1992, now abandoned. The contents of these applications are incorporated herein by reference.

TECHNICAL FIELD

The invention relates to the metabolic effects of a class of glutathione analogs interactive with at least one glutathione S-transferase class. More particularly, the invention is directed to modulation of hematopoiesis in bone marrow or blood and to other useful responses to this class of glutathione S-transferase inhibitors.

BACKGROUND ART

The side effects of chemotherapeutic agents used in the treatment of malignancy and other indications are well known. Among these side effects are alterations in the levels of various blood cells, including neutrophils, platelets and lymphocytes. The results of these effects can be neutropenia, thrombocytopenia and immune suppression generally. These side effects are not only unpleasant, but they also restrict the efficacy of cancer therapy and place the subject at serious risk of infection and uncontrolled bleeding.

At the present time, there appears to be little practical remediation for these effects. Some approaches are merely palliative, such as supportive care. Others have their own side effects, such as large doses of antibiotics. Still others are expensive and invasive such as transfusions. Still another approach, the administration of growth factors, such as granulocyte colony-stimulating factor (GCSF), granulocyte macrophage colony-stimulating factor (GMCSF), and more newly developed factors such as megakaryocyte growth and development factor (MGDF) and thrombopoietin (TPO) are costly and must be administered by injection. They also have their own associated negative side effects.

Clearly there is a need for a simpler approach, for example a small molecule drug, preferably administerable by mouth, that can protect and restore bone marrow and also stimulate the production of neutrophils, platelets and lymphocytes both in conjunction with chemotherapeutic protocols and in response to other factors which result in hematopoietic suppression such as cyclic and idiopathic neutropenias, thrombocytopenia, and the effects of allograft transplants.

The problems related to current approaches for managing the side effects of chemotherapy and otherwise dealing with suppression of hematopoiesis are solved at least in part by the biological activity of certain simple tripeptide compounds which are inhibitors of the various isoenzymes of glutathione S-transferase.

PCT application WO95/08563 published Mar. 30, 1995, and based on PCT/US94/10797, from which the parent application herein claims priority, discloses these tripeptide compounds which are analogs of glutathione. They are generally inhibitors of glutathione S-transferase activity and the various compounds contained in this group show diverse specificities with respect to glutathione S-transferase isoenzymes.

A subset of these analogs, which is of the general formula

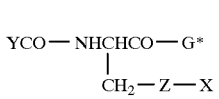

(1)

and the amides and esters thereof, wherein YCO is γ-glu or β-asp; G* is phenylglycine or glycine; Z is CH$_2$, O or S; and X is a hydrocarbon radical of 1–20C, have now been found to have the ability to modulate hematopoiesis in bone marrow and in peripheral blood and therefore exert protective effects when chemotherapeutic agents destructive to the hematopoietic system are administered. These compounds also potentiate the desired effects of chemotherapeutic agents. This same subset of glutathione analogs shows inhibition of the π class of glutathione S-transferase (GST), and, in some cases, other classes as well.

DISCLOSURE OF THE INVENTION

The invention provides compounds which are useful in modulating hematopoiesis generally and as aids to chemotherapeutic treatment of tumors by virtue of their ability to exert a protective effect on the hematopoietic system with respect to toxic agents which are otherwise useful in chemotherapy. The compounds are orally active and can be used in any context where it is desirable to modulate the hematopoietic processes in bone marrow or peripheral blood or to modulate other bone marrow processes.

Thus, in one aspect, the invention is directed to a method to modulate hematopoiesis from progenitor cells which method comprises contacting bone marrow or peripheral blood, or fractions of these containing progenitors with a compound of the formula

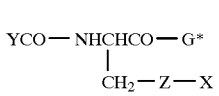

(1)

or the ester, amide, ester/amide or salt forms thereof, wherein YCO is γglu or β-asp;

G* is phenylglycine or glycine;

Z is CH$_2$, O or S; and

X is a hydrocarbon radical of 1–20C;

in an amount and for a time effective to modulate hematopoiesis in said bone marrow, peripheral blood or fraction.

In another aspect, the invention is directed to a method to exert a protective effect against the destructive effects of a chemotherapeutic agent, including irradiation, administered to a subject, said protection including the mode of action whereby acceleration of recovery from such effects occurs, which method comprises administering the compound of formula (1) to said subject in an amount and for a time effective to exert said protective effects.

In other aspects, the invention is directed to methods and formulations for promoting the production of neutrophils, platelets and lymphocytes, restoring damaged bone marrow, protecting bone marrow from cytotoxic therapy, and exerting a protective effect as against neutropenia, thrombocytopenia, lymphocytopenia and anemia caused by chemotherapy, infection or hematological diseases and for the expansion of cell populations in the course of bone marrow transplantation. The invention is further directed to the use of compounds of the invention as tumor-specific chemo- or radiosensitizers, thus potentiating the effect of treatment, and as generalized chemoprotectants.

The invention also includes pharmaceutical compositions containing the compounds of the invention as active ingredients, and methods for synthesis of the invention compounds.

In still another aspect, the invention is directed to a method to modulate hematopoiesis or to exert a protective effect against the destructive effects of a chemotherapeutic agent which method comprises contacting bone marrow, peripheral blood, or a suitable fraction thereof with a compound which inhibits glutathione S-transferase isoenzymes of at least one class, and generally inhibits GST of the π class at a reasonable level.

BRIEF DESCRIPTION OF THE DRAWINGS

FIGS. 13A and 12B are graphs showing the effect of TER199 on cyclophosphamide-induced GM-CFU suppression in mice.

FIG. 16A shows myeloid progenitor differentiation (CFU-GEMM) and FIG. 16B shows erythroid progenitor generation (BFU-E). The $CD34^{+++}$ cells were purified from human cord blood and were plated at a concentration of 300 cells/ml.

MODES OF CARRYING OUT THE INVENTION

Figure 1B:
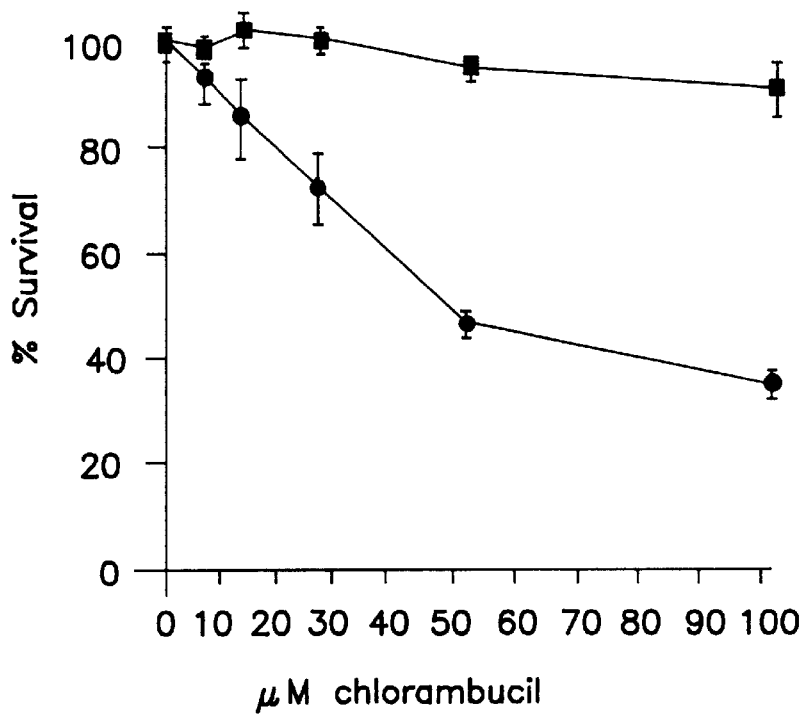
FIG. 1b shows the toxic effect of TER199 in contrast to its unesterified form on HT4-1 cells.

Many of the compounds useful in the methods of the invention inhibit the activity of at least one isoenzyme subclass of the glutathione S-transferase isoenzymes. These compounds also modulate hematopoiesis in bone marrow, even in the presence of agents which ordinarily would destroy a large percentage of the cells needed to sustain hematopoeisis, as well as exhibiting other helpful effects on bone marrow and blood cells. These compounds are of the formula

(1)

wherein YCO, G*, Z and X are defined as above. When used in vivo, or in vitro for the purpose of affecting intact cells, the compounds of the invention are preferably in the amide, ester or hybrid amide/ester forms.

It will be apparent that the compounds of the invention may be present as the free acids, salts, monoesters, diesters, monoamides, diamides or hybrid ester/amide forms. The amides and esters useful in the invention are generally those of alkyl (1–10C); alkenyl (1–10C); and arylalkyl (7–12C) alcohols and amines. Thus, typical esters and amides useful in the invention include dimethyl esters, diethyl esters, mixed ethyl/propyl esters, dihexyl esters, mixed hexyl/octyl esters, dibutenyl esters, mixed butenyl/vinyl esters, the corresponding amides, and the like. Especially preferred are the diethyl ester forms of the compounds of formula (1). A preferred embodiment of Z is O or S, particularly S; and a preferred embodiment of YCO is γ-glu.

Preferred embodiments for the hydrocarbon (1–20C) moiety of X include hexyl, heptyl, octyl, benzyl and naphthyl.

Particularly preferred compounds of the invention are γE-C (octyl)-φG; γE-C(Hx)-φG; γE-C(naphthyl)-φG; γE-C(Bz)-φG; and γE-C(octyl)-G; γE-C(Hx)-G; and γE-C(Bz)-G; and especially their diesters, and more preferably their diethyl esters. Particularly preferred are γE-C(Bz)-φG diethyl ester (TER199) and γE-C(octyl)-G diethyl ester (TER183).

It will be evident that the tripeptides of the invention contain one or two chiral centers. The designations set forth above are directed to the genus of diastereomers which result from the presence of these chiral centers. Particularly preferred, however, are those embodiments wherein the amino acid represented by YCO (γ-glu or β-asp) is in the native, L configuration; the cysteine or cysteine analog residue represented by NHCH(CH$_2$ZX)CO is also in the native, L, configuration, and when G* is phenylglycine, the phenylglycine is preferably in the D configuration. Thus, preferred compounds of the invention where G* is phenylglycine are the LLL and LLD forms, especially the LLD form It is recognized that depending on the nature of "X", additional chiral centers may be included.

The compounds of the invention have several properties which make them useful as adjuncts to chemotherapy and other indicators. First, they modulate hematopoiesis in bone marrow, the destruction of which is a common side-effect of chemotherapeutic agents. Second, they usually inhibit at least one class of the GST isoenzymes, including the π subclass, which is particularly prevalent in tumor cells. Third, the compounds of formula (1) directly potentiate the effect of chemotherapeutic agents in the destruction of tumor cells. This combination of qualities makes the compounds of the invention useful both as hematopoiesis potentiating agents directly and to ameliorate the negative effects of chemotherapeutic protocols, as well as enhancing the toxic effect to the target cells. When formulated for use in vivo or in contact with intact cells, the compounds of formula (1) will preferably be supplied as the esters, preferably the diesters, more preferably the diesters of saturated alcohols containing 1–5C, more preferably 1–3C, and most preferably as the diethyl esters.

The synthesis of the tripeptides of the invention can be accomplished by standard methods well known in the art. Specific techniques for synthesis of the tripeptides of the invention are set forth in the above-referenced PCT application WO95/08563. A particularly preferred route of synthesis is described in the present application.

Administration and Use

By "modulating hematopoiesis in bone marrow or peripheral blood" is meant altering the rate of blood cell formation as measured by the capacity to form colonies or differentiated cells. Differentiated cells include neutrophils, platelets, red blood cells, lymphocytes, macrophage, granulocytes, granulocyte-macrophage and the like. It is unclear what the mechanism of this modulation is; the cells themselves may or may not be directly stimulated by the compounds of the invention; rather, the change in number and/or size of colonies of differentiated cells may be due to preferential survival, inhibition of apoptosis, or any one of a number of factors. As used in the present application, "modulating hematopoiesis in bone marrow or peripheral blood" refers to the ability of bone marrow or blood treated with the compounds of the invention to exhibit colony formation or generation of differentiated cells at a level different from that of untreated bone marrow. Similarly, fractions of bone marrow or peripheral blood which contain suitable progenitors will exhibit this effect. It should be noted, that as used herein, "peripheral blood" specifically includes cord blood.

In addition to modulating hematopoiesis, the compounds of the invention affect bone marrow cells directly and exert a beneficial effect on bone marrow cells other than those of hematopoietic origin. For example, these compounds also enhance the formation of osteoblasts so as to aid in bone regeneration. Thus, their beneficial effects on bone marrow are not limited to modulation of hematopoiesis per se.

In general, when agents are employed which typically have destructive effects on bone marrow or on hematopoiesis in blood, the compounds of the invention exert a protective effect. By "protective effect" is meant that the resultant damage to the bone marrow or blood is less when the compound is administered than when it is not. The net decrease in damage may be due to protection per se—i.e., preventing the destructive effects that would normally occur or may result from accelerating recovery from such destruction. Thus, "protective effect" includes the effect of achieving this desirable result regardless of the mechanism by which it is achieved.

There are a number of situations in which the protective effect of the compounds of the invention are useful. These include instances where irradiation has resulted, or may result prospectively, in negative effects, instances where a subject is immunocompromised for any reason, instances wherein a subject exhibits damage to the kidneys, as well as instances wherein the subject has been subjected to chemotherapy. In addition, the compounds of the invention may be used in transplantation settings to increase the number of cells in the bone marrow of a donor; typically, in this case the compound may be administered in vivo or ex vivo. In this setting also, the compounds of the invention promote the movement of progenitor cells into the peripheral blood of the donor which thus improves the recovery of peripheral blood white cell numbers in this donor; similarly, the compounds of the invention may improve the recovery of peripheral white blood cell numbers in the recipient. In general, the compounds will improve expansion and promote the eventual engraftment of transplanted cells after exposure to the compounds of the invention in vivo or ex vivo. The compounds of the invention can be used directly in the recipient to hasten recovery.

In addition, patients subjected to kidney dialysis are aided by the compounds of the invention in reconstituting blood. The compounds are also useful in encouraging bone growth generally.

The compounds of the invention can be used either in vitro or in vivo. For example, these compounds can be employed to expand or otherwise modulate hematopoietic cells in bone marrow prior to allogeneic or xenogeneic transplants. Treatment of subjects using ex vivo techniques whereby expansion of relatively undifferentiated cells from the blood stream may also be employed. The compounds of the invention can also be formulated for in vivo administration.

When ex vivo administration is employed, either bone marrow or peripheral blood (including cord blood) or both can be directly contacted with the invention compounds or fractions of these materials may be treated so long as the fractions contain suitable target progenitor cells. Preferred target progenitor cells include CD34$^+$ cells, GEMM, and BFU-E.

Formulations for in vivo administration will employ standard methods such as those described in *Remington's Pharmaceutical Sciences*, latest edition, Mack Publishing Company, Easton, Pa. The compounds may be formulated for injection, for oral administration, or for alternative methods of administration such as transmucosal or transdermal administration. Injection can be intravenous, intraperitoneal, intramuscular, or by any other conventional route. As shown hereinbelow, the compounds of the invention are effective when administered orally as well as when introduced directly into the blood stream or when administered i.p.

Since oral administration is particularly convenient, and since the compounds of the invention are active when administered orally, formulations suitable for administration by mouth are particularly preferred. Such formulations include, as is well understood, pills, tablets, capsules, syrups, powders, or flavored liquids. The various formulations can be prepared in unit dosage form and can, if desired, be self-administered by the subject. The percentage of active ingredient compound (or mixture of compounds) in the formulation may vary over a wide range from about 0.5% w/w to about 95% w/w. The preferred percentage of active ingredient will be dependent on the nature of the formulation per se. Suitable excipients included in these formulations include fillers, buffering agents, stabilizers and the like.

For administration, if desired, by injection, preferred formulations include balanced physiological solutions and liposomal compositions.

Suitable subjects who will benefit from administering the compounds of the invention, either a single compound or mixtures thereof, include vertebrate subjects, particularly mammalian or human subjects whose bone marrow progenitor cells are inadequate in number or physiological status to sustain differentiation differentiate inappropriately. Failure of progenitor cells to result in required numbers of effector cells occurs, in particular, when the subject has been exposed to bone marrow destructive agents, such as chemotherapeutic agents, radiation, exposure to toxins in the environment and the like. Also included are those with bone marrow degenerative diseases and conditions. Thus, appropriate subjects for administration of the invention compounds include patients undergoing chemotherapy; immunocompromised patients, patients showing symptoms of anemia, neutropenia, thrombocytopenia, or lack of adequate platelet levels, and prospective subjects for treatment with cytotoxic agents. As the compounds of the invention also potentiate the cytotoxicity of chemotherapeutic agents with respect to malignant cells specifically, subjects may benefit from treatment with the compounds of the invention even though the hematopoietic system is not necessarily compromised by the chemotherapeutic treatment.

As stated above, a single compound of the invention may be included as active ingredient or the treatment may comprise use of mixtures of these compounds. In addition, the compounds of the invention may be mixed with or used in addition to other beneficial agents such as immunostimulants or growth factors.

The dosage required depends on the nature of the subject, the nature of the condition, the manner of administration, and the judgment of the attending physician or veterinarian. Suitable dosage ranges are adjusted according to these parameters. In general, typical doses per patient will be in the range of 0.1–100 mg/kg per day for 10–40 days, more preferably 1–10 mg/kg per day for 14–28 days. These ranges are merely illustrative and the correct dosage optimization can be determined by routine methods.

If the invention compounds are administered as protective agents with regard to chemotherapeutic treatment, the timing of administration may also be relevant. The timing will, however, depend on the nature of the chemotherapeutic agent used. As shown below, for example, when 5 FU is used for chemotherapy, administration seems advantageous about 24 hours subsequent to administration of the 5 FU; on the other hand, although this timing of administration is also effective when cisplatin is the chemotherapeutic agent, administration about 24 hours prior to cisplatin dosing is more effective. It is clearly within routine skill to determine appropriate timing for the specific chemotherapeutic agent employed.

Illustrative Compounds

As illustrative compounds useful as GST isoenzyme inhibitors, the following were prepared:
γE-C(Bz)-φG (TER117);
γE-C(hexyl)-φG (TER102);
γE-C(naphthyl)-G (TER211); and
γE-C(octyl)-G (TER143).

Among these compounds, TER117 showed the highest specificity for GST P1-1. TER102 was also reasonably specific. Therefore, various derivatives of TER117 were synthesized. In all of the foregoing compounds, the γ-glutamyl and cysteinyl residues are present in their native L configurations; in TER117 and TER102, phenylglycine is in the D configuration.

The following esters and amides of TER117 were prepared:
TER199: γE ethyl ester-C(Bz)-R-(-)-φG ethyl ester;
TER278: γE ethyl amide-C(Bz)-R-(-)-φG ethyl amide; and
TER300: γE ethyl amide-C(Bz)-R-(-)-φG ethyl ester.

The in vitro half-life of TER199 in mouse blood is less than 1 minute, while the half-life in human blood is approximately 90 minutes.

In vitro studies of these compounds showed that TER278 and TER300 have longer half-lives than TER199 in mouse blood and in HT-29 cell culture; however, the half-life in human blood for all three compounds is approximately the same.

TER278 is less toxic and less able to potentiate chlorambucil than is TER199.

TER300 is metabolized at a rate intermediate between that of TER199 and TER278 in mouse blood and in HT-29 cell culture. Four times as much TER300 as TER199 is required to achieve equivalent potentiation of chlorambucil. The following examples are intended to illustrate, but not to limit, the invention.

EXAMPLE 1

Use of the Compounds of the Invention in Potentiation of Cytotoxic Agents in Human Cells This example describes: 1) potentiation in human tumor cells of a cytotoxic agent currently used in cancer chemotherapy by GST inhibitors, including compounds of the present invention, as well as 2) enhanced intracellular efficacy of esterified forms of these compounds.

HT-29 (human colon adenocarcinoma) cells were obtained from Dr. Roberto Ceriani (Cancer Research Fund of Contra Costa County, Walnut Creek, Calif.) and were used in log phase of growth unless otherwise specified. Chlorambucil (CMB) was obtained from Sigma (St. Louis, Mo.) and was dissolved in 100% ethanol. All GST inhibitors were dissolved in ethanol, DMSO, or water just prior to use. The same amount of solvent added to culture medium served as the vehicle control.

In a modified clonogenic assay for cytotoxicity, cells were suspended at $2 \times 10^5$ cells/ml in serum-free medium in the presence of vehicle or inhibitor. Inhibitors were used at concentrations that resulted in ≦90% survival in the presence of inhibitor alone, when compared to vehicle treated cells. Cells were incubated for 2 hours, then varying doses of CMB were added. At the end of a second 2-hour incubation, cells were diluted to $7.5–10 \times 10^3$/ml in serum-containing medium and plated in quadruplicate at 200 μl/well in Microtest III microtiter plates.

Plates were incubated for 6 days and assayed by a modified methylene blue method. Briefly, cells were fixed with 1.25% glutaraldehyde in PBS then stained with 0.05% methylene blue in distilled water. Plates were washed several times in distilled water to remove unretained dye and retained dye was resolubilized in 0.03 N HCl. Plates were read at 650 nm in a Molecular Devices Vmax plate reader (Molecular Devices, Redwood City, Calif.). $IC_{50}$ values (inhibitor concentration causing 50% reduction in cell viability) were determined for the drug in the presence or absence of inhibitor from dose-response curves. A dose modification factor (DMF), a measure of potentiation of cytotoxicity, was calculated for each inhibitor by dividing the $IC_{50}$ value of CMB without inhibitor treatment by the $IC_{50}$ value for CMB with inhibitor treatment.

The results in Tables 1–3 show that several GSH analogs found to be inhibitors of GSH also potentiate killing of human tumor cells in culture by CMB which is a substrate for various GSTs. Results of potentiation tests with several GST inhibitors in HT29 cell cultures are summarized in Table 1.

TABLE 1

Potentiation of Chlorambucil Cytotoxicity in Human Cells by GST Inhibitors and Their Esters

| | Parent Compound | | Diethyl ester | |
|---|---|---|---|---|
| GST Inhibitor | Dose tested[a] (μM) | DMF[b] | Dose tested[b] (μM) | DMF[b] |
| γE-C(octyl)-G | N.D. | — | 5 | 0.86 ± 0.02 |
| γE-C(Hx)-φG | 100 | 1.1 ± 0.02 | 12.5 | 1.27 ± 0.02 |
| γE-C(Bz)-φG | 100 | 1.08 ± 0.01 | 12.5 | 1.65 ± 0.04 |
| γE-C(naphthyl)-G | 200 | | 12.5 | 1.21 ± 0.01 |

[a]Test dose was determined from toxicity curve and analogs were used at the dose at which ≧90% survival occurred in the presence of the analog alone.
[b]Dose modification factor. Values are mean ± S.D. of 2–3 experiments.

As shown in Table 1, this potentiation is greatly enhanced by esterification which is designed to enhance uptake of the GST inhibitors. Thus, γE-C(Bz)-φG at 100 μM did not enhance cell killing by CMB, reducing the concentration CMB needed for 50% cell killing by a DMF of 1.08. In contrast the diethyl ester of γE-C(Bz)-φG (TER 199) at only 12.5 μM enhanced CMB cytotoxicity by a factor of 1.65.

Preferential expression of GST isoenzyme P1-1 has been reported in a range of human tumors. In the present study the efficacy of CMB potentiation of the several GST inhibitors tested correlated directly with their potencies as inhibitors of the human π class GST isoenzyme, P1-1, as shown in Table 2.

TABLE 2

Rank Correlation of Chlorambucil Dose Modification Factors (DMFs) of GST Inhibitors with $K_i$ value for Inhibition of Human GST P1-1

| Rank Inhibitor | Relative Ki value of parent compound | Rank order | DMF[a] of DEE |
|---|---|---|---|
| γE-C(Bz)-φG | 1 | 1 | 1.651 |
| γE-C(Hx)-φG | 2.1 | 2 | 1.272 |
| γE-C(naphthyl)-G | 3 | 3 | 1.213 |
| γE-C(octyl)-G | 4.8 | 4 | 0.864 |

[a]Dose modification factor of diethyl ester. Values are mean ± S.D. of 2–3 experiments.

The effect of esterification or amidation of the compounds of Formula (1) on their potentiation of chlorambucil cytotoxicity in HT-29 cells was also determined. The DMF was determined for the diethyl ester, the diamide, and the ester/amide of γE-C(Bz)-φG at relevant concentrations. The diester showed a DMF of 1.65±0.04 for chlorambucil toxicity at 12.5 μM; the diamide showed a DMF of 1.0 in a single experiment at 200 μM; the ester/amide hybrid showed a DMF of 1.45±0.16 at 50 μM concentration. The results for the diethyl ester and the ester/amide hybrid are given as the mean ± SD of three experiments.

Diethyl esters of γE-C(octyl)-G (TER183) and γE-C(Bz)-φG (TER199) were tested in a standard clonogenic assay using three cell lines: HT4-1, a subclone of HT-29; SKOV-3 an ovarian carcinoma, and VLB, a vinblastine-resistant variant of SKOV-3. Four chemotherapeutic drugs, chlorambucil, adriamycin, mitomycin C and doxorubicin were used as the toxic agents. In these assays, the cells were seeded at 300 cells/well in 2 ml of medium in 6-well plates in the presence of the compounds of the invention as the diethyl esters. The compounds were used at concentrations that resulted in more than 85% survival when compared to controls. After incubation for 1–2 hours to permit cells to attach, varying doses of the chemotherapeutic agents were added. At least three replicate wells were plated for each test condition and the plates were incubated for two weeks. Colonies were fixed in 95% ethanol and stained with crystal violet for colony counting. $IC_{50}$ values were determined for the chemotherapeutic agent in the presence or absence of the compound of the invention and dose modification factors were calculated by dividing the $IC_{50}$ value of drug without the invention compound by the $IC_{50}$ value of the drug with the invention compound. The modification factors obtained in each protocol are shown in Table 3.

TABLE 3

Ability of selected GSH analogs to potentiate drug toxicity as demonstrated in a clonogenic assay

| | | DMF[a] for: | | | |
|---|---|---|---|---|---|
| Cell Line | GSH Analog | Chlorambucil | Adriamycin | Mitomycin C | Doxorubicin |
| HT4-1 | TER199 | 2.39 | 1.2 | 1.03 | 1.20 |
| | TER183 | 1.74 | 1.13 | 1.56 | n.d.[d] |
| SKOV-3 | TER199 | 1.24 | 1.14 | 1.03 | 1.14 |
| | TER183 | 1.03 | 1.24 (@5 uM)[c] | n.d.[b] | n.d.[d] |
| VLB | TER199 | N.D.[d] | 2.50 | 0.82 (5 μM TER199)[c] | 2.50 |
| | TER183 | N.D.[d] | 1.06 | 1.63 | n.d.[d] |

[a]Dose modification factor.
[b]No data due to toxicity of analog.
[c]Test dose was different from listed at the left.
[d]Not determined.

As shown in Table 3, significant modification was obtained when chlorambucil was used as the drug versus HT4-1 cells in the presence of 25 μM of TER199. Significant modification was also achieved in VLB cells when treated with adriamycin or doxorubicin in the presence of 25 μM of the same compound.

Figure 1A:
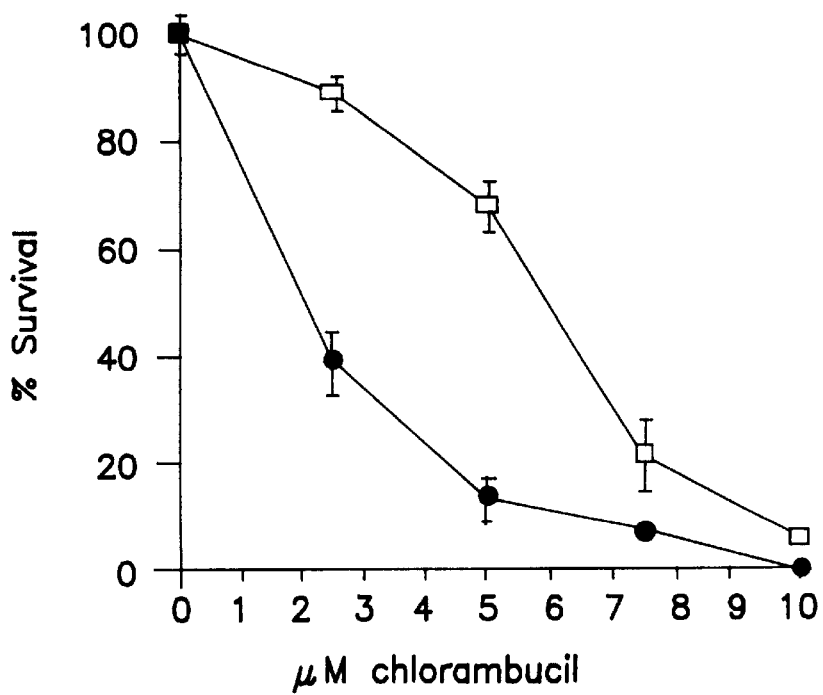
FIG. 1a shows the effect of TER199 on the survival of tumor cells treated with various concentrations of chlorambucil.

FIG. 1a illustrates the results for varying dosages of chlorambucil and the modifying effect of 25 μM of the diethyl ester of γE-C(Bz)-φG (TER199). The open squares (□) represent chlorambucil alone, the closed circles (●) chlorambucil in the presence of the invention compound. As seen in FIG. 1a, the survival rate is markedly diminished when the invention compound is added. FIG. 1b confirms that the diethyl ester is necessary to penetrate the cells. HT4-1 cells were tested for survival in the presence of either γE-C(Bz)-φG (TER117) (closed squares, ■) or its diethyl ester (TER199) (closed circles, ●). The unesterified form, TER177, has substantially no effect on these cells while the diethyl ester (TER199) is clearly toxic.

EXAMPLE 2

Potentiation of Melphalan Toxicity in vivo

Male scid mice were subcutaneously implanted with HT4-1 tumors from donor mice. HT4-1 is a subclone of HT-29, a human colon cancer. When tumors reached approximately 100 mm³, the mice were randomized into six treatment groups and treated for seven days as follows:

1. 5 mg/kg melphalan;
2. 10 mg/kg ethacrynic acid;
3. 60 mg/kg TER199;
4. 5 mg/kg melphalan+10 mg/kg ethacrynic acid;
5. 5 mg/kg melphalan+60 mg/kg TER199;
6. vehicle alone.

The mice were monitored for weight changes and tumor volumes were determined by measurement with calipers. The tumor growth was monitored until the average tumor size reached 1500 mm³ for all groups except melphalan with ethacrynic acid. This group failed to reach this volume even after 72 days.

The results were computed in terms of the tumor volume in the drug treated mice as a percentage of control tumor volume (i.e., in the group administered vehicle alone). In group 1, administered melphalan alone, the tumors were approximately 75% of the volume of controls. In group 5 when TER199 was administered along with the melphalan, the tumor volume mean was approximately 55% of control. For group 4 administered a combination of melphalan and ethacrynic acid, the volumes were approximately 35% of control. Thus, both ethacrynic acid and TER199 potentiate the effects of melphalan. (The volume measurements were taken at the time control tumors reached 1500 mm³.)

EXAMPLE 3

Metabolic Effects of the Invention Compounds

The metabolic effects related to toxicity of the compounds of the invention on HT-29 cells, were tested using a Cytosensor Microphysiometer made by Molecular Devices, Inc., Menlo Park, Calif. and described in McConnell, H. M. et al. *Science* (1992) 257:1906–1912 and by Wada, H. G. et al. *AATEX* (1992) 1:154–164. Changes in pH of the culture medium are measured as a function of cellular metabolism. Acidification rates of the small volume of liquid flowing over the cells correlate with the number of live cells in the reaction chamber; a reduction of acidification rate reflects reduced numbers of surviving cells.

In this illustration, HT-29 cells were plated at $4 \times 10^5$ cells/chamber in a medium containing 10% fetal calf serum. After 16–18 hours the serum level was reduced to 1% and the cells were maintained for another 18 hours. Cells were then exposed to either ethacrynic acid (50 $\mu$M), TER199 (20 $\mu$M) or a vehicle (0.1% ethanol) for 4 hours. The medium was then replaced with serum-free low buffer capacity medium and Microphysiometer analysis was initiated. Half of the chambers were exposed to 100 $\mu$M chlorambucil and the other half to vehicle (0.1% ethanol). Acidification rates were monitored for 16 hours and the data are expressed as percentage of the basal (100%) acidification rates.

Figure 2:
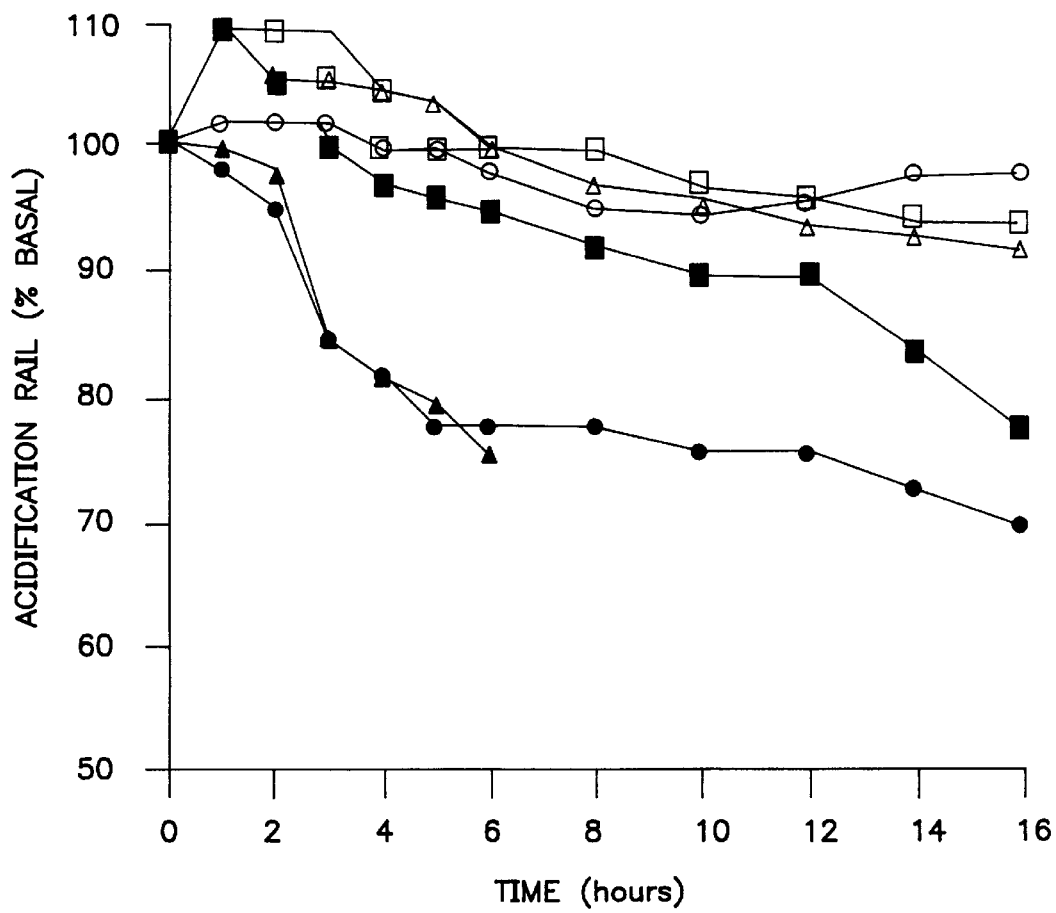
FIG. 2 is a graph showing the effect of various combinations of chlorambucil either alone or in combination with ethacrynic acid or TER199.

The results are shown in FIG. 2. Neither γE-C(Bz)-φG diethylester (TER199) nor ethacrynic acid alone had any appreciable effect on acidification rates; however, both ethacrynic acid pretreatment and pretreatment with the TER199 potentiated the effect of chlorambucil. In the figure, the open symbols reflect no addition of chlorambucil; the closed symbols reflect addition of chlorambucil; the squares reflect the pretreatment with vehicle, triangles pretreatment with ethacrynic acid, and circles pretreatment with TER199.

EXAMPLE 4

Stimulation of Bone Marrow Granulocyte Macrophage (GM) Progenitors

Figure 3:
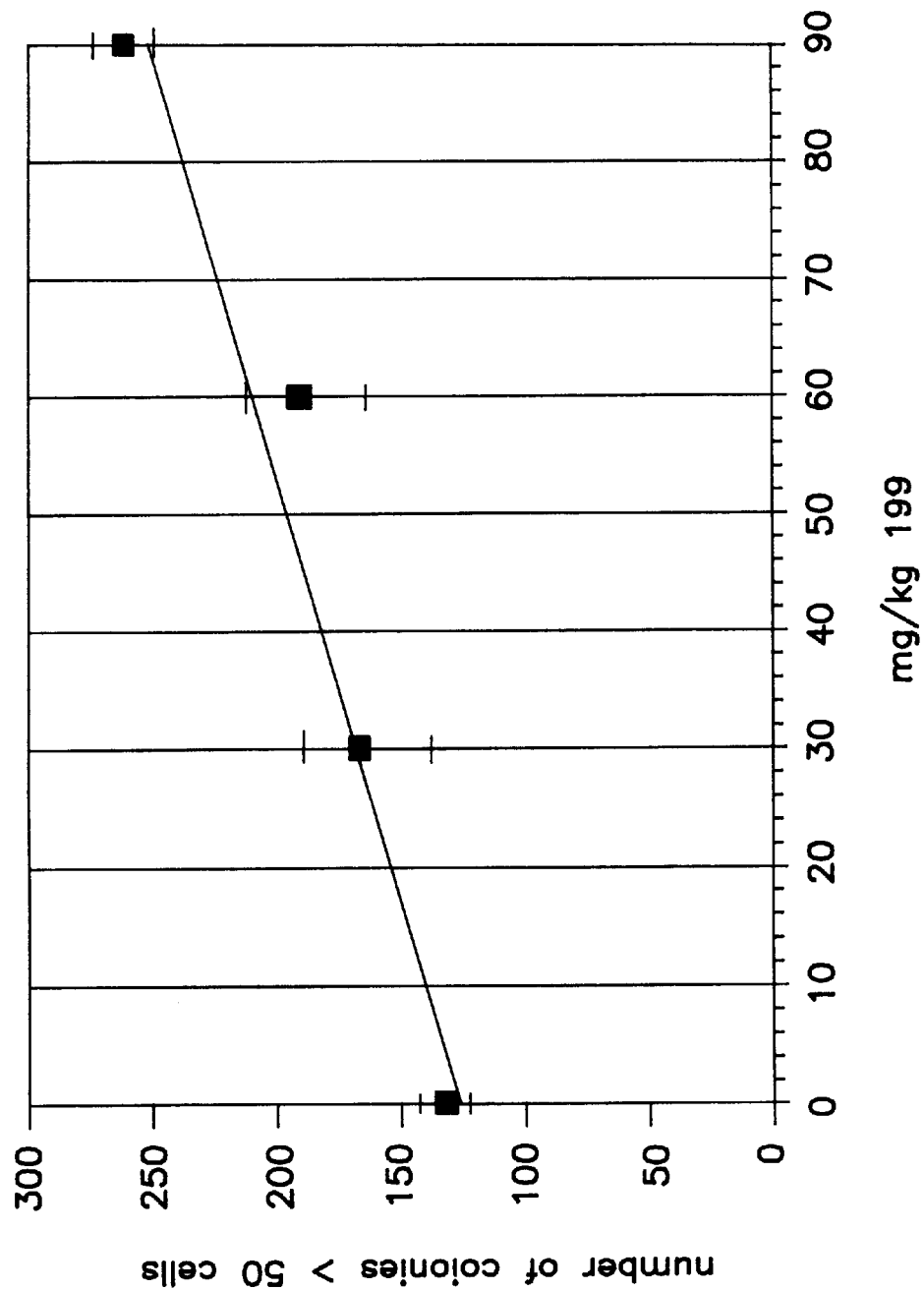
FIG. 3 is a graph showing the dose-dependent effect of TER199 on mouse GM-CFU 24 hours posttreatment. The points represent the mean ± standard deviation of three mice.

The compounds of the invention, when esterified so as to be able to penetrate cells, also stimulate the production of GM progenitors in bone marrow when administrered to mammalian subjects. In an illustrative assay three $B6D2F_1$ mice were treated with various doses of benzyl PG intraperitoneally. Femoral bone marrows were harvested 24 hours later and assayed for GM-CFU by the method of East, C. J. et. al. *Cancer Chemother Pharmacol* (1992) 31:123–126. An increase in the number of colonies in a dose-dependent manner up to a dosage of 90 mg/kg of TER199 was obtained. These results are shown in FIG. 3. At 90 mg/kg, approximately 275 colonies/$10^4$ nucleated cells were obtained compared to about 140 colonies/$10^4$ nucleated cells for controls.

EXAMPLE 5

Comparison of Intraperitoneal and Oral Administration of TER199 on Mouse GM-CFU

Male $B6D2F_1$ mice, five weeks old, 20–24 grams were divided into groups of three mice and administered various dosages of TER199 either orally or intraperitoneally. The TER199 was prepared in sterile nanopore water and administered orally using a gavage tube and a 1 cc syringe or intraperitoneally in saline using a 1 cc syringe with a 28 gauge needle. Mice in the control group were injected with water or saline. Bone marrow cells were harvested 24 hours after drug treatment and added to alpha minimum essential medium (alpha MEM) supplemented with methylcellulose (0.8% w/v), fetal bovine serum (20% v/v), deionized BSA (1% w/v), Pokeweed mitogen-stimulated spleen-cell conditioned medium (PWM-SCCM)[1] (10% v/v) and gentamycin (50 Tg/ml). One ml aliquots were plated (four replicate plates) and incubated for seven days at 370 C. A dissecting microscope was used to count the granulocyte/macrophage colonies having more than 50 cells per colony (GM-CFU).

[1] Pokeweed mitogen-stimulated spleen cell condition medium (PWM-SCCM) was prepared according to the procedure of Gringeri et al., 1988. Spleens were removed aseptically from four male $B6D2F_1$ mice enforced through a 200 Tm wire mesh screen to obtain a single cell suspension. Ten ml of the suspension (2–4×10$^7$ cell/ml was added to 90 ml alpha-MEM supplemented with 1% deionized BSA, 50 Tg/ml gentamicin, 0.3% freshly reconstituted pokeweed antigen, 10 $\mu$M 2-mercaptoethanol. The mixture was incubated for 5 days at 370° C. in a 5% $Co_2$ atmosphere and the resulting conditioned medium was centrifuged at 800 g for ten minutes and filtered through a 0.22 Tm filter. Aliquots were kept frozen at −200° C. until use.

Figure 4A:
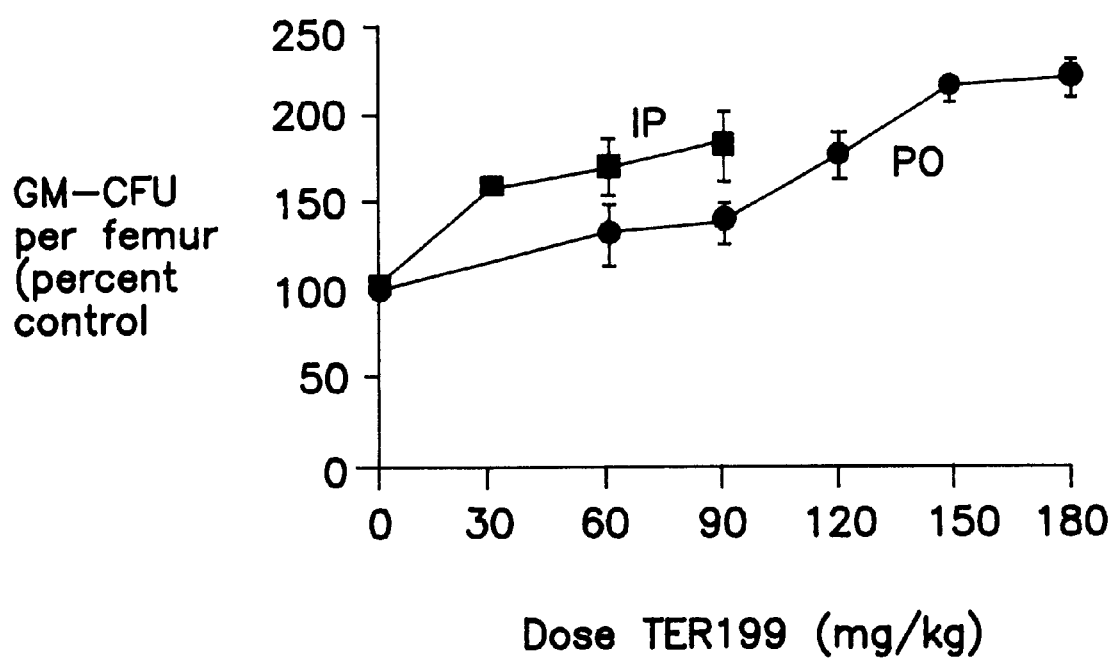
FIG. 4a is a graph showing the comparison of oral versus IP administration of TER199 on bone marrow GM-CFU.

FIG. 4a shows the effect of oral versus IP administration of TER199 on bone marrow GM-CFU in a single treatment. The data are mean ± SEM for three mice per group. The asterisk indicates that the value is statistically significant from the control, P<0.05. As shown in FIG. 4a, IP administration (closed squares, ■) is most effective at 60–90 mg/kg; oral administration (closed circles (●) is most effective at 120–180 mg/kg. The results show that the compounds of the invention may be administered orally as well as IP, although higher dosage levels may be required for oral administration.

Figure 4B:
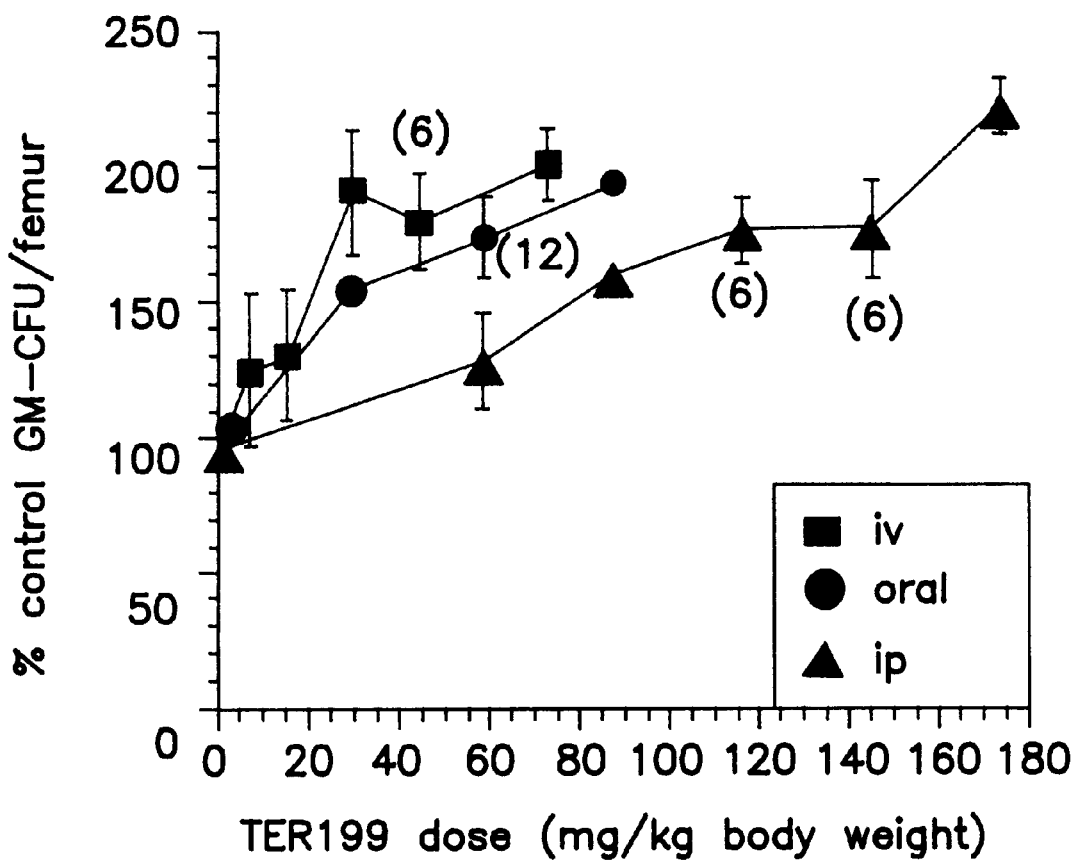
FIG. 4b is a graph showing the comparison of oral versus IV administration of TER199 on bone marrow GM-CFU. Each point represents the mean ± standard error of each group. The parenthetical numbers are the number of mice per group. For all other points, n=3.

FIG. 4b shows results of an additional experiment and includes administration IV. Similar results are obtained.

EXAMPLE 6

Time Course of TER199 Stimulation of Bone Marrow Macrophage (GM) Progenitors

Figure 5:
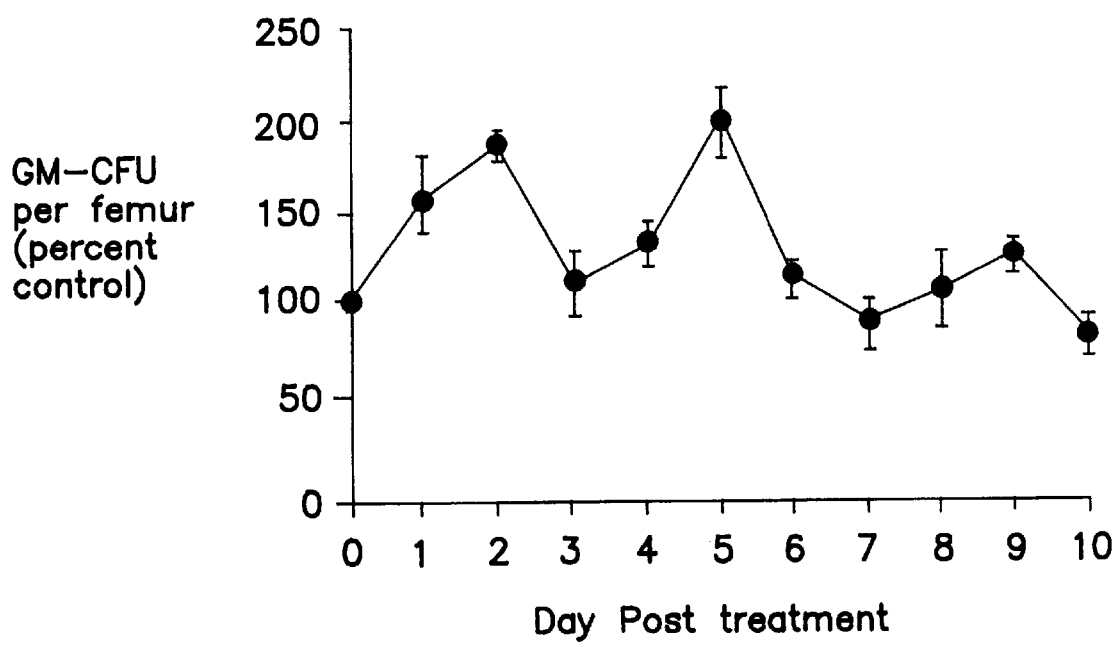
FIG. 5 shows the time course of TER199 stimulation of GM-CFU administered IP.

The procedures of Example 5 were repeated using a single 60 mg/kg dose of TER199 administered IP on day 0 and harvesting bone marrow cells at various times after administration. The GM-CFU for the mice administered TER199 was compared to controls, and the results are shown as a function of day after administration in FIG. 5. Maximum stimulation appeared to occur at day 2 and day 5.

EXAMPLE 7

TER199 Effect on Mouse and Human Bone Marrow Colony Formation

The effect of TER199 on colony formation by granulocyte-macrophage (CFU-GM), erythroid (BFU-E), and multipotential (CFU-GEMM) progenitor cells was evaluated. TER199 enhances the proliferation of human and murine myeloid progenitor cells in vitro. The effects are dose-dependent, usually in the range of 1.0 to 10.0 μM, and in most cases for cells stimulated by GM-CSF, G-CSF, M-CSF, Flt3/Flk-2 and Steel factor (stem cell factor/c-kit ligand). Of particular interest was the finding that TER199 enhances colony formation stimulated by combinations of cytokines. Additionally, the enhancing effect is more pronounced in human than in murine bone marrow. These results suggest that TER199 has enhancing effects on multiple lineages of myeloid stem cells and progenitors. That there is a greater effect on human marrow is consistent with the specificity of TER199 for the human GST isozyme P1-1. Results from a representative set of these experiments are presented in Tables 4–9.

TABLE 4

Influence of TER199 on colony formation by normal human bone marrow GM-progenitor cells stimulated by single cytokines.

| Growth Factor (Per ml) | Colony Number (% Change)* | | | | Colony & Cluster Number (% Change)* | | | |
|---|---|---|---|---|---|---|---|---|
| | Control Medium | TER199 (0.1 μM) | TER199 (1 μM) | TER199 (10 μM) | Control Medium | TER199 (0.1 μM) | TER199 (1 μM) | TER199 (10 μM) |
| None | 0 | 0(–) | 0(–) | 1 ± 1 (–) | 22 ± 1 | 22 ± 2 (0) | 49 ± 2 (123) | 51 ± 5 (132) |
| GM-CSF (10U) | 29 ± 1 | 28 ± 2 (–3) | 35 ± 1 (21)* | 39 ± 3 (34)* | 54 ± 1 | 54 ± 1 (0) | 75 ± 3(39) | 81 ± 6 (50) |
| GM-CSF (100U) | 56 ± 3 | 53 ± 1 (–5) | 60 ± 1 (7) | 70 ± 2 (25)* | 80 ± 2 | 73 ± 2 (–9) | 84 ± 2 (5) | 90 ± 3 (13)* |
| G-CSF (10U) | 14 ± 2 | 14 ± 1 (0) | 20 ± 1 (43)* | 23 ± 2 (64)* | 26 ± 1 | 28 ± 2 (8) | 39 ± 2 (50)* | 42 ± 4 (62)* |
| G-CSF (100U) | 19 ± 2 | 17 ± 1 (–10) | 17 ± 2 (–10) | 25 ± 1 (32)* | 33 ± 2 | 29 ± 2 (–12) | 31 ± 2 (–6) | 42 ± 1 (27)* |
| IL-3 (10U) | 12 ± 1 | 13 ± 1 (8) | 21 ± 2 (75)* | 26 ± 1 (117)* | 37 ± 1 | 35 ± 2 (–5) | 62 ± 8 (68)* | 59 ± 5 (59)* |
| IL-3 (100U) | 39 ± 5 | 38 ± 3 (–2) | 37 ± 2 (–5) | 52 ± 1 (33)* | 63 ± 6 | 58 ± 1 (–8) | 64 ± 4 (2) | 81 ± 2 (29)* |
| M-CSF (100U) | 2 ± 0.3 | 3 ± 1 (50) | 3 ± 0.3 (50) | 5 ± 0.6 (150)* | 19 ± 3 | 26 ± 4 (37) | 37 ± 0.3 (95)* | 49 ± 3 (158)* |
| M-CSF (1000U) | 4 ± 0.3 | 8 ± 1 (100)* | 10 ± 1(150)* | 11 ± 1 (175)* | 41 ± 4 | 43 ± 3 (5) | 52 ± 3 (27)* | 65 ± 6 (59)* |
| Flt3-L (100ng) | 11 ± 3 | 19 ± 3 (73)* | 20 ± 1 (82)* | 23 ± 3 (109)* | 28 ± 4 | 48 ± 1 (71)* | 55 ± 3 (96)* | 57 ± 4 (104)* |
| SLF 50ng) | 28 ± 2 | 44 ± 1 (57)* | 41 ± 2 (46)* | 43 ± 5 (54)* | 45 ± 2 | 72 ± 2 (60)* | 65 ± 4 (44)* | 67 ± 5 (49)* |

*Statistically significant

TABLE 5

Influence of TER199 on colony formation by normal human bone marrow GM-progenitor cells stimulated by combinations of cytokines

| Growth Factors (per ml) | Colony Number (% Change)* | | | |
|---|---|---|---|---|
| | Control Medium | TER199 (0.1 μM) | TER199 (1 μM) | TER199 (10 μM) |
| Flt-3 (100 ng) + 100 U GM-CSF | 77 ± 1 | 95 ± 5 (23)* | 114 ± 7 (48)* | 115 ± 5 (49)* |
| Flt-3 (100 ng) + 100 U G-CSF | 32 ± 4 | 41 ± 55 ± | 51 ± 77 ± | 48 ± 77 ± |
| Flt-3 (100 ng) + 100 U IL-3 | 3 | 2 (0) | 3 (40)* | 2 (40)* |
| Flt-3 (100 ng) + 50 ng SLF | 38 ± 4 | 62 ± 2 (63)* | 77 ± 3 (103)* | 77 ± 4 (103)* |
| SLF (50 ng) + 100 U GM-CSF | 92 ± 5 | 92 ± 5 (0) | 121 ± 7 (32)* | 125 ± 5 (136)* |
| SLF (50 ng) + 100 U G-CSF | 40 ± 3 | 41 ± 2 (3) | 55 ± 5 (38)* | 58 ± 5 (45)* |
| SLF (50 ng) + 100 U IL-3 | 60 ± 2 | 77 ± 4 (28)* | 103 ± 10 (72)* | 109 ± 4 (82)* |

*Statistically significant

Only colonies formed when Flt3-L or SLF were added together or with GM-CSF, G-CSF, or IL-3.

TABLE 6

Influence of TER199 on colony formation by normal human bone marrow erythroid (BFU-E) and multipotential (CFU-GEMM) progenitor cells

| Growth Factors Added (per ml) | Colony Number (% Change from Control) | | | |
|---|---|---|---|---|
| | Control Medium | TER199 (0.1 μM) | TER199 (1.0 μM) | TER199 (10 μM) |
| BFU-E | | | | |
| None | 0 | 0 | 0 | 0 |
| Epo (1 U) | 36 ± 6 | 35 ± 3 (6) | 60 ± 2 (82)* | 57 ± 4 (73) |
| Epo (1 U) + 100 U IL-3 | 48 ± 5 | 47 ± 3 (-2) | 62 ± 4 (29)* | 65 ± 7 (35)* |
| Epo (1 U) + 50 ng SLF | 88 ± 4 | 92 ± 4 (5) | 107 ± 7 (22)* | 109 ± 2 (24)* |
| CFU-GEMM | | | | |
| None | — | — | — | — |
| Epo (1 U) | — | — | — | — |
| Epo (1 U) + 100 U IL-3 | — | — | — | — |
| Epo (1 U) + 50 ng SLF | 22 ± 2 | 19 ± 2 (-14) | 23 ± 2 (5) | 30 ± 1 (36)* |

*Statistically significant

TABLE 7

Influence of TER199 on colony and cluster formation by normal BDF$_1$ mouse bone marrow granulocyte-macrophage (CFU-GM) progenitor cells.

| Growth Factor (Per ml) | Colony Number (% Change)* | | | | Colony & Cluster Number (% Change)* | | | |
|---|---|---|---|---|---|---|---|---|
| | Control Medium | TER199 (0.1 μM) | TER199 (1 μM) | TER199 (10 μM) | Control Medium | TER199 (0.1 μM) | TER199 (1 μM) | TER199 (10 μM) |
| None | 0 | 0 | 0 | 0 | 0 | 0 | 0 | 0 |
| GM-CSF (10U) | 9 ± 0.6 | 10 ± 2(11) | 13 ± 0.3(11) | 13 ± 0.7(44) | 72 ± 1 | 72 ± 4(0) | 80 ± 2(11)* | 81 ± 2 (13)* |
| GM-CSF (100U) | 65 ± 4 | 62 ± 4(-5) | 80 ± 1(23)* | 71 ± 0.3(9) | 74 ± 5 | 71 ± 3(-4) | 91 ± 0.3(23)* | 84 ± 0.5(14)* |
| M-CSF (10U) | 0 | 0 | 0 | 0 | 9 ± 1 | 9 ± 1(0) | 24 ± 0.6(167)* | 26 ± 2(189)* |
| M-CSF (100U) | 44 ± 2 | 43 ± 1(-2) | 67 ± 5(52)* | 63 ± 6(43)* | 247 ± 6 | 247 ± 3(0) | 304 ± 17(23)* | 259 ± 8(5) |
| PWMSCM† (10% v/v) | 72 ± 2 | 74 ± 5(3) | 118 ± 3(64)* | 110 ± 4(53)* | 117 ± 1 | 115 ± 9(-2) | 172 ± 2(47)* | 157 ± 1(34)* |

*Statistically significant
†PWMSCM = Pokeweed mitogen stimulated spleen cell conditioned medium

TABLE 8

Influence of TER199 on colony formation by normal human bone marrow erythroid (BFU-E) and multipotential (CFU-GEMM) progenitor cells

| | Colony number (% change from control) | | | |
|---|---|---|---|---|
| TER199 (μM) | 0 | 0.1 | 1.0 | 10 |
| BFU-E: | | | | |
| EPO 1 U/ml | 33 ± 6 | 35 ± 3 (6) | 60 ± 2 (82)* | 57 ± 4 (73) |
| | 42 ± 4 | 38 ± 3 (-10) | 58 ± 1 (38)* | 59 ± 2 (31)* |
| EPO + 50 ng/ml SLF | 88 ± 4 | 92 ± 4 (5) | 107 ± 7 (22)* | 109 ± 2 (24)* |
| | 66 ± 3 | 80 ± 5 (21)* | 80 ± 3 (35)* | 85 ± 3 (29)* |
| CFU-GEMM: | | | | |
| | 22 ± 2 | 19 ± 2 (-14) | 23 ± 2 (5) | 30 ± 1 (36)* |
| EPO + 50 ng/ml SLF | 10 ± 2 | 12 ± 1 (20) | 17 ± 2 (70)* | 16 ± 1 (60)* |

*Significant increase compared to control, $p < 0.05$

TABLE 9

Influence of TER199 on colony formation by normal BDF$_1$ mouse bone marrow erythroid (BFU-E) and multipotential (CFU-GEMM) progenitor cells

| | Colony number (% change from control) | | | |
|---|---|---|---|---|
| TER199 (μM) | 0 | 0.1 | 1.0 | 10 |
| BFU-E: | | | | |
| EPO 1 U/ml | 2 ± 1 | 2 ± 1 (0) | 2 ± 1 (0) | 2 ± 1 (0) |
| | 4 ± 1 | 4 ± 1 (0) | 3 ± 1 (-25) | 4 ± 1 (0) |
| EPO + 50 ng/ml SLF | 7 ± 1 | 8 ± 1 (14) | 8 ± 1 (14) | 8 ± 1 (14) |
| | 9 ± 1 | 9 ± 1 (0) | 9 ± 1 (0) | 9 ± 1 (0) |
| CFU-GEMM: | | | | |
| | 2 ± 1 | 2 ± 1 (0) | 2 ± 1 (0) | 2 ± 1 (0) |
| EPO + 50 ng/ml SLF | 2 ± 1 | 2 ± 1 (0) | 1 ± 1 (-50) | 2 ± 1 (0) |

Tables 8 and 9 show the results of an experiment designed to compare the results obtained when TER199 was contacted with human bone marrow erythroid and multipotential progenitor cells as opposed to their murine counterparts. As shown in these tables, the effects ex vivo in humans (Table 8) are substantially greater than those exhibited in their murine counterparts (Table 9).

EXAMPLE 8

Effect of TER199 on Peripheral Blood Cells

Figure 6:
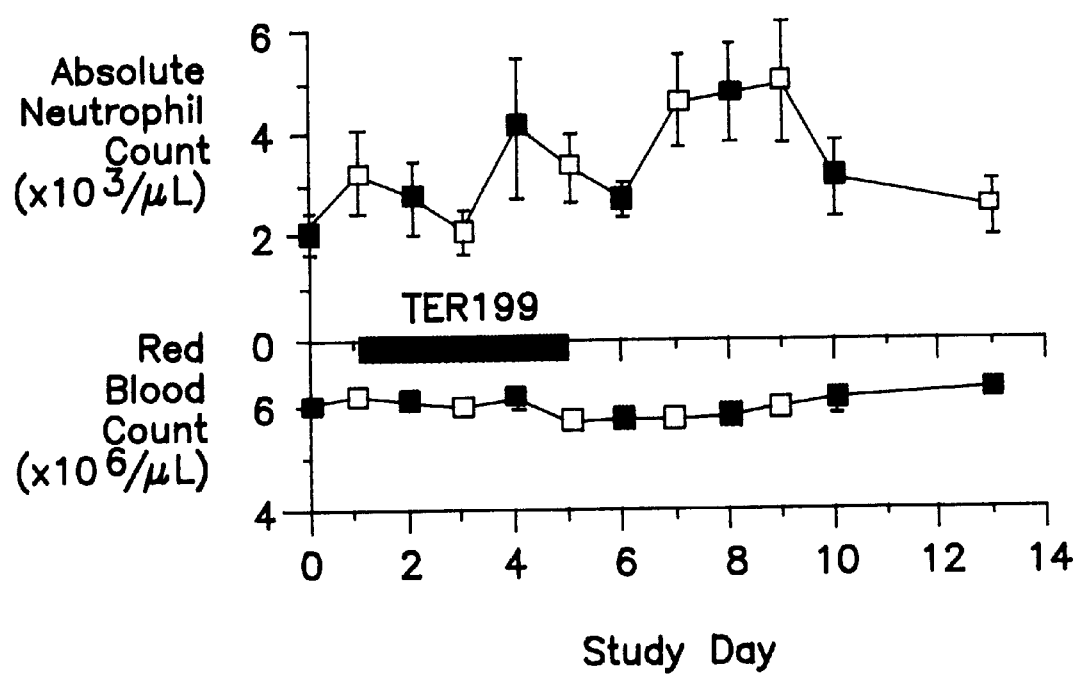
FIG. 6 is a graph showing the effect of TER199 on neutrophil and red blood cell counts.

The effect of TER199 (90 mg/kg/day×5, i.p.) on peripheral blood counts was evaluated in Sprague-Dawley derived rats. Rats were divided into two groups and each group was bled on alternating days. Mean total leukocyte, absolute lymphocyte and absolute neutrophil counts increased over the study period. Representative data are presented in FIG. 6. TER199 causes a twofold increase in the levels of circulating white blood cells in rats. There was no significant change in red blood cell or platelet counts with the exception of a mean decrease in platelet count on day 9 (data not shown). In addition, TER199 did not appear to have any deleterious effects on these animals.

EXAMPLE 9

Structural Requirements

Figure 7:
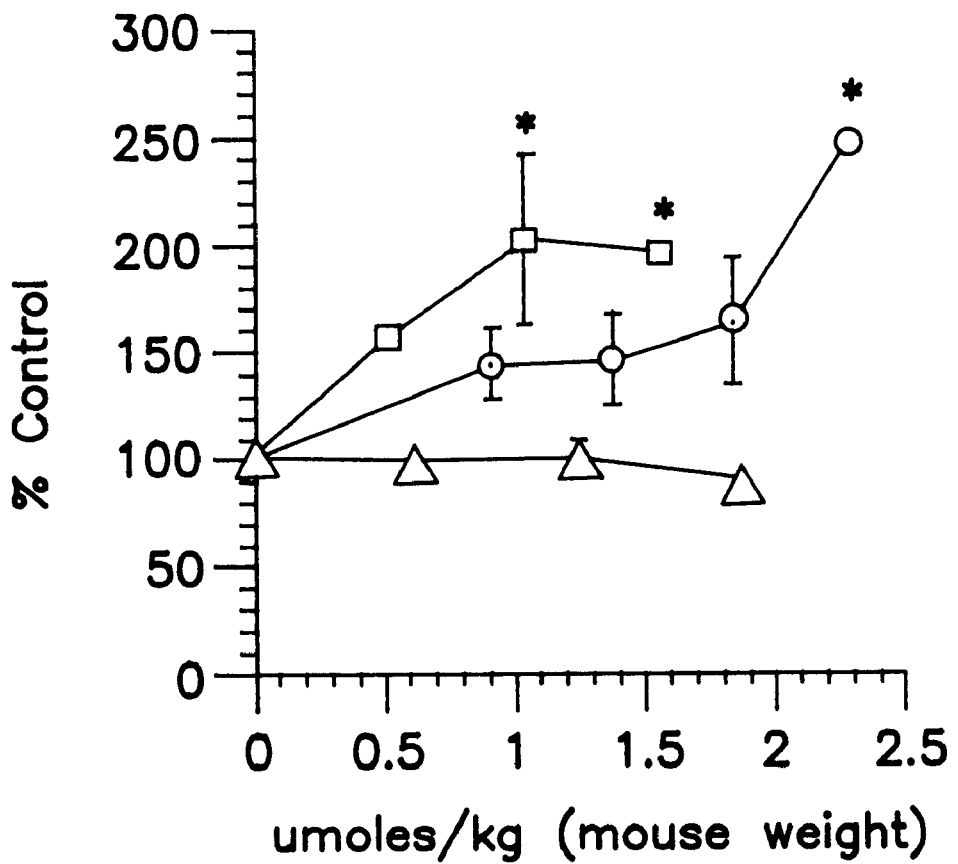
FIG. 7 is a graph showing the dependence of the esterified or amidated form of the tripeptides with respect to GM-CFU stimulation.

The effect on bone marrow differentiation by various derivatives and structural analogs of TER199 as a function of dosage level was also determined. Bone marrow was harvested 24 hours after administering the compounds and GM-CFU levels measured as described above. FIG. 7 shows that the diethyl ester (TER199) is significantly more effective than the mixed ester amide (TER300) in that the corresponding unesterified compound is not effective. In FIG. 7, the open triangles (Δ) represent the unesterified compound (TER117); the open circles (○) represent the mixed ester amide (TER300). The open squares (□) represent the results with the diethyl ester, TER199. The mixed ester amide, TER300 is known to be metabolized more slowly than TER199. Metabolism of TER300 produces TER117. The results in FIG. 7 are consistent with the inability of TER117 to enter the cells and the slower metabolism of TER300.

Figure 8:
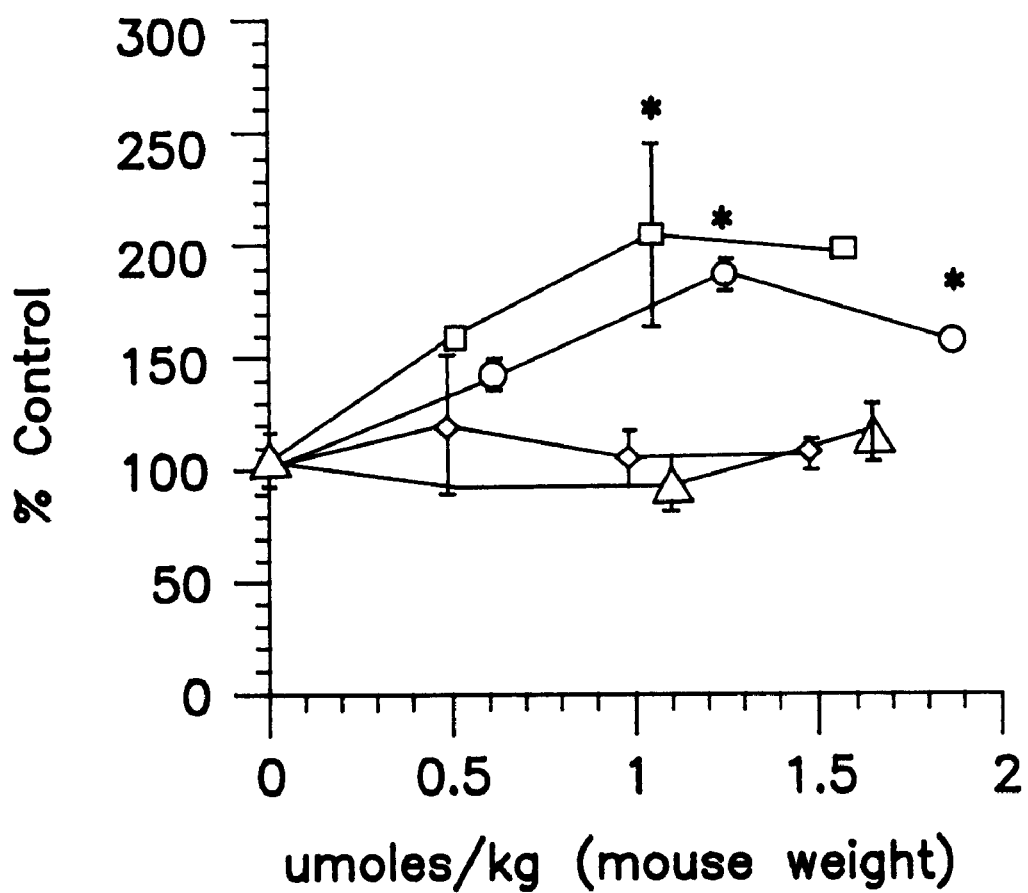
FIG. 8 is a graph showing the effect of the nature of the "X" substituent of Formula 1 on stimulation of GM-CFU.

FIG. 8 shows results of similar experiments for TER199 and its analogs. The open squares (□) represent TER199; open circles (○) represent TER183 where the benzyl group in TER199 is replaced by octyl and φG by G. The open diamonds (◇) and open triangles (Δ) represent the inactive compounds TER317 and TER206, respectively; in TER317, phenylglycine of TER199 is replaced by (S+)phenylalanine; in TER206 the benzyl of TER199 is replaced by naphthyl and phenylglycine by glycine. These results correlate with the targeting of P1-1 GST isoenzyme by TER199 and TER183 as shown in Table 10, although TER183 is a better inhibitor of A1-1 than of P1-1.

TABLE 10

Structure, GST $K_i$ Values and bone marrow differentiation enhancement effect for glutathione analogs

| TER | Structure | Ki ($\mu$M)* | | | | BMDE** |
|---|---|---|---|---|---|---|
| | | P1-1 | A1-1 | M1a-1a | M2-2 | |
| 199 | γE-C(Bz)-φG | 0.4 | 20 | 25 | 31 | + |
| 183 | γE-C(octyl)-G | 1.9 | .27 | 1.2 | n.d. | + |
| 317 | γE-C(Bz)(S+)-fA | >10³ | >10³ | >10³ | >10³ | − |
| 206 | γE-C(naphthyl)-G | 1.2 | 4.2 | .01 | 1.5 | − |

*determined on unesterified form
**bone marrow differentiation enhancement

EXAMPLE 10

TER199 Amelioration of the Effect of Chemotherapeutic Agents a) Effect of a single i.p. dose of TER199 on GM-CFU suppression caused by 5-fluorouracil.

Figure 9A:
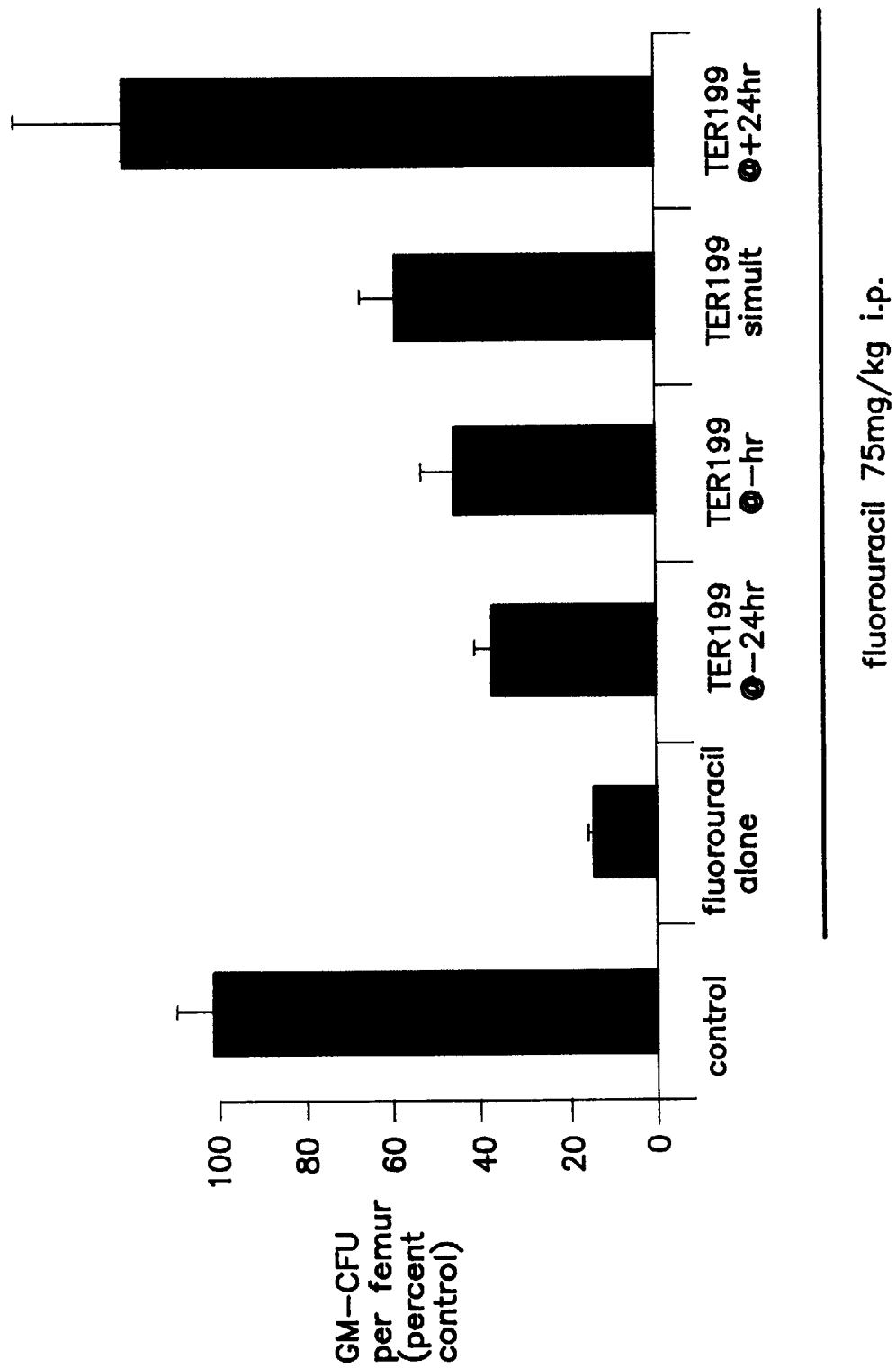
FIG. 9a is a graph showing the effect of TER199 on 5-fluorouracil (5-FU) GM-CFU supression in mice.

The male $B62F_1$ mice described in Example 5 were administered 75 mg/kg of 5-fluorouracil (5-FU) prepared in 0.9% sterile saline and administered IP. Mice in groups of three were injected IP with 60 mg/kg TER199 in sterile water either simultaneously with 5-FU administration, 24 hours before, 1 hour before or 24 hours after 5-FU administration. The control group was not treated with either drug. Bone marrows were harvested and GM-CFUs were determined 24 hours after the final injection. Consensus results are shown in FIG. 9a. TER199 @−24 hr.; @−1 hr; and @+24 hr means TER199 was given 24 hours before, 1 hour before or 24 hours after 5-FU, respectively. 5-FU treatment alone reduces the GM-CFU to 15% of control mice. TER199 significantly decreases the 5-FU-induced GM-CFU suppression. Simultaneous injection of TER199 with fluorouracil results in a fourfold increase in the number of GM-CFUs per femur as compared with injection of fluorouracil alone. Injection of TER199, 24 hours after fluorouracil, results in greater than control values of GM-CFU counts per femur.

Figure 9B:
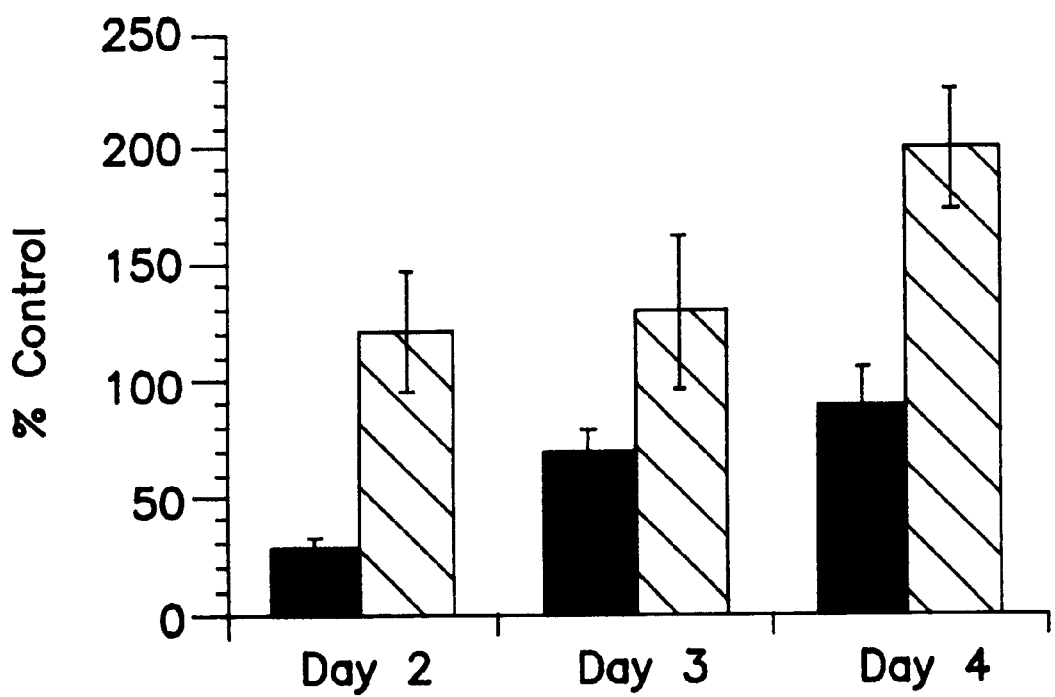
FIG. 9b is a graph showing the time-course effect of IP administration of TER199 24 hours after administration of 5-FU on the recovery of the differentiation ability of bone marrow cells.
Figure 9C:
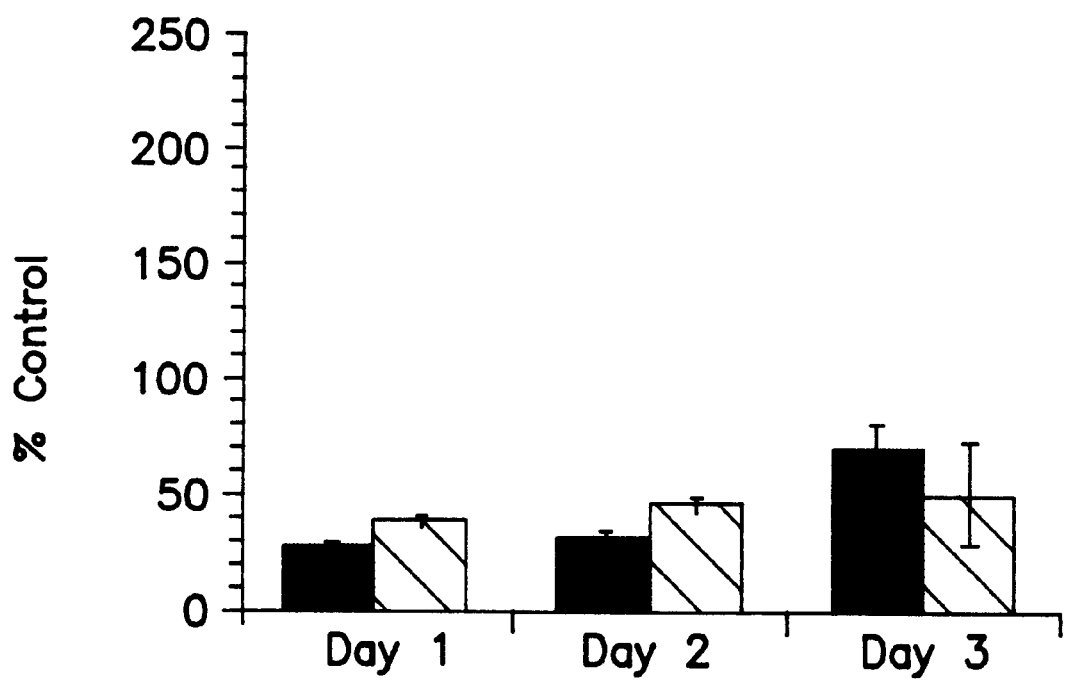
FIG. 9c is a graph showing the effect of pretreatment with TER199 (i.p.) on 5-FU-induced GM-CFU suppression.

Administration of TER199 as described above 24 hours after administration of 5-FU hastened the recovery of bone marrow cells and resulted ultimately in stimulation of this capability above controls not administered 5-FU. These results are summarized in FIG. 9b which shows that by day 4 after 5-FU administration, mice administered 5-FU only (closed bar, ■) showed GM-CFU approximately equal to control while those which had received TER199 in addition to 5-FU (hatched bar, ▓) showed GM-CFU about twice that of control. Similar experiments but administering TER199 24 hours prior to 5-FU had essentially no effect on GM-CFU as shown in FIG. 9c.

b) Effect of a single oral dose of TER199 on GM-CFU suppression caused by 5-fluorouracil.

Figure 9D:
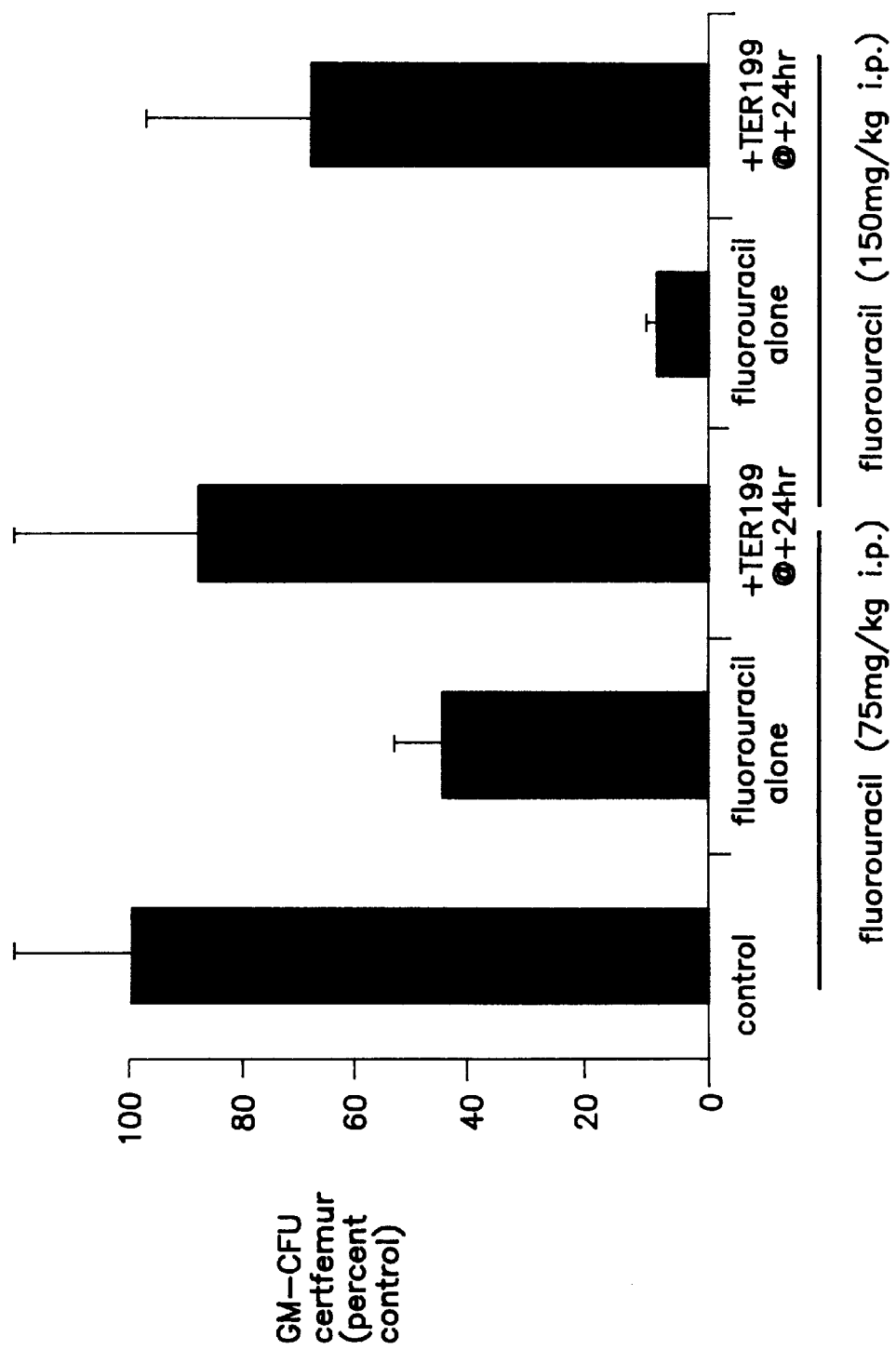
FIG. 9d is a graph comparing the effects of oral and IP administration of TER199 24 hours after administration of 5-FU on GM-CFU suppression in mice.

The effects of TER199 administered 24 hours after injection of 5-FU by an IP route were also obtainable when the TER199 was administered orally. Bone marrow was harvested 48 hours after administering 75 or 150 mg/kg 5-FU by IP. When administered 24 hours after 5-FU (75 or 150 mg/kg i.p.), TER199 (150 mg/kg p.o.) causes a twofold increase in GM-CFU at the lower dose of 5-FU (90% vs 47% of control), and a ninefold increase with the higher dose (71% vs 8%); see FIG. 9d. Values are the mean ± SE of three mice per point.

c) Effect of TER199 on GM-CFU suppression caused by cisplatin.

Figure 10:
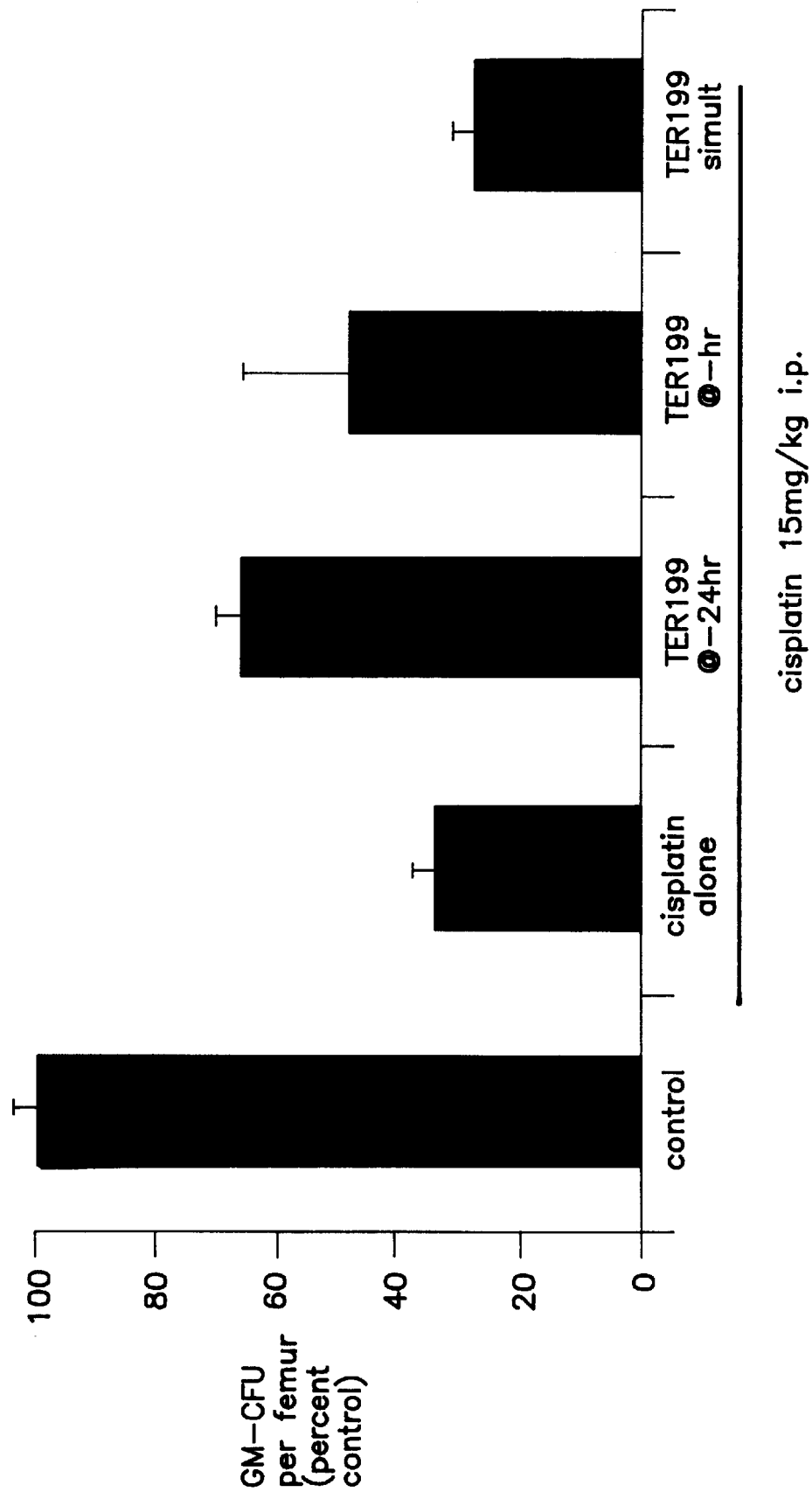
FIG. 10 is a graph showing the effect of TER199 on cisplatin (i.p.)-induced GM-CFU suppression in mice.

The effect of a single p.o. or i.p. dose of TER199 was evaluated for its ability to reduce cisplatin-induced GM-CFU supression in mice. TER199 (60 mg/kg i.p.) was administered 24 hours before, one hour before, or simultaneously with cisplatin (15 mg/kg i.p.). Bone marrows were harvested 24 hours after cisplatin administration. GM-CFU values are the mean ± SE of three mice per point. FIG. 10 shows that prior administration of TER199 increases GM-CFUs compared to administration of cisplatin alone (FIG. 10). Injection of TER199 24 hours before cisplatin results in a twofold increase in the number of GM-CFUs per femur as compared with injection of cisplatin alone (62% vs 31% of control).

Figure 11:
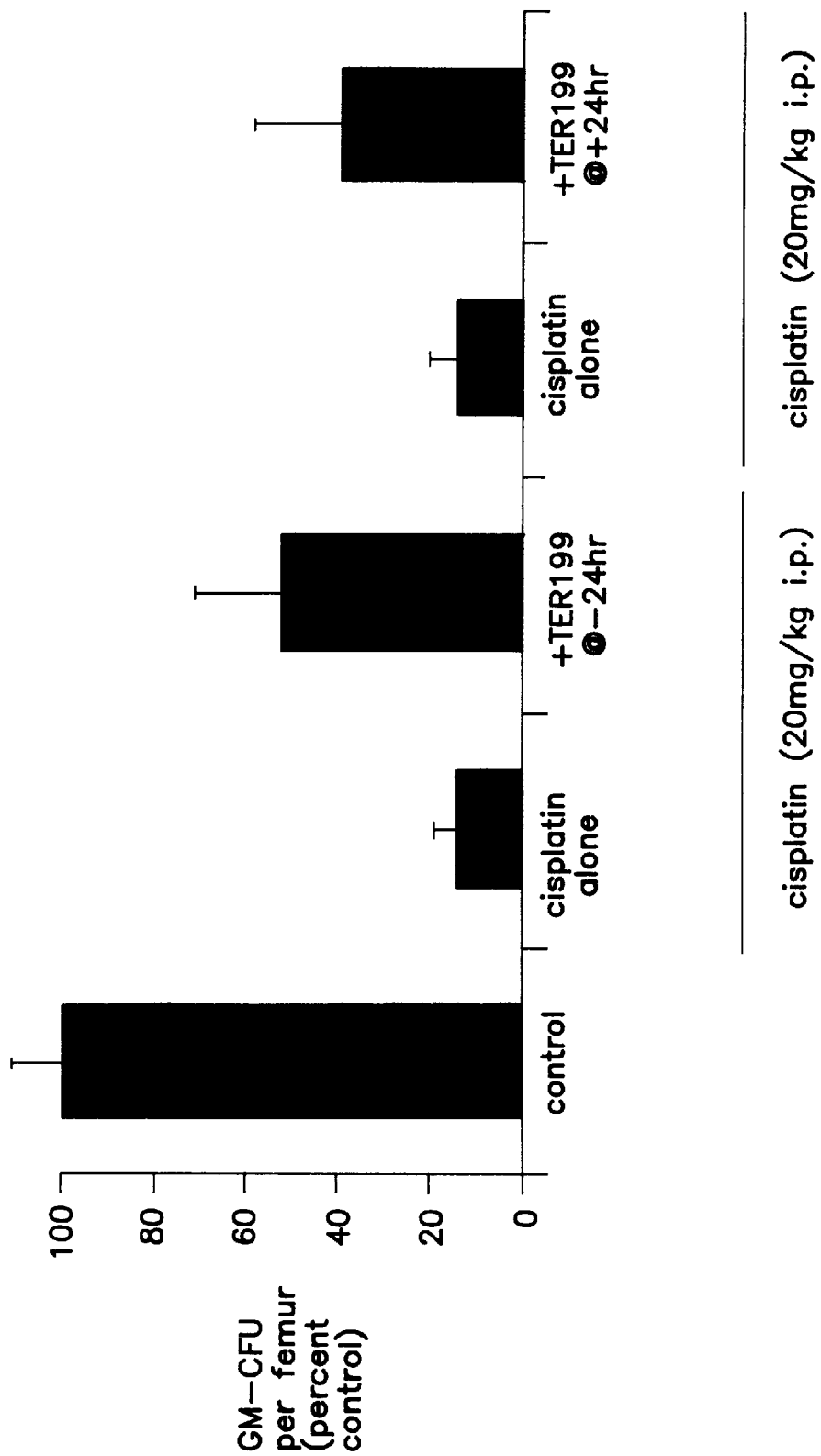
FIG. 11 is a graph showing the effect of oral TER199 cisplatin-induced GM-CFU suppression in mice.

The experiment presented in FIG. 11 shows the effect of oral administration of TER199 24 hours pretreatment or 24 hours posttreatment on cisplatin induced GM-CFU suppression. Bone marrows were harvested 24 hours after administration of the second drug. Values are the mean ± SE of three mice per point. When administered orally 24 hours before cisplatin (20 mg/kg i.p.), TER199 (150 mg/kg p.o.) results in nearly a fourfold increase in GM-CFU (52% vs 14% of control). Administration of TER199 24 hours after cisplatin results in a 2.5-fold increase in GM-CFU (40% vs 14%). These results indicate TER199 may be useful in the prevention and treatment of cisplatin-induced neutropenia.

d) Effect of TER199 on carboplatin-induced GM-CFU suppression in mice.

Figure 12A:
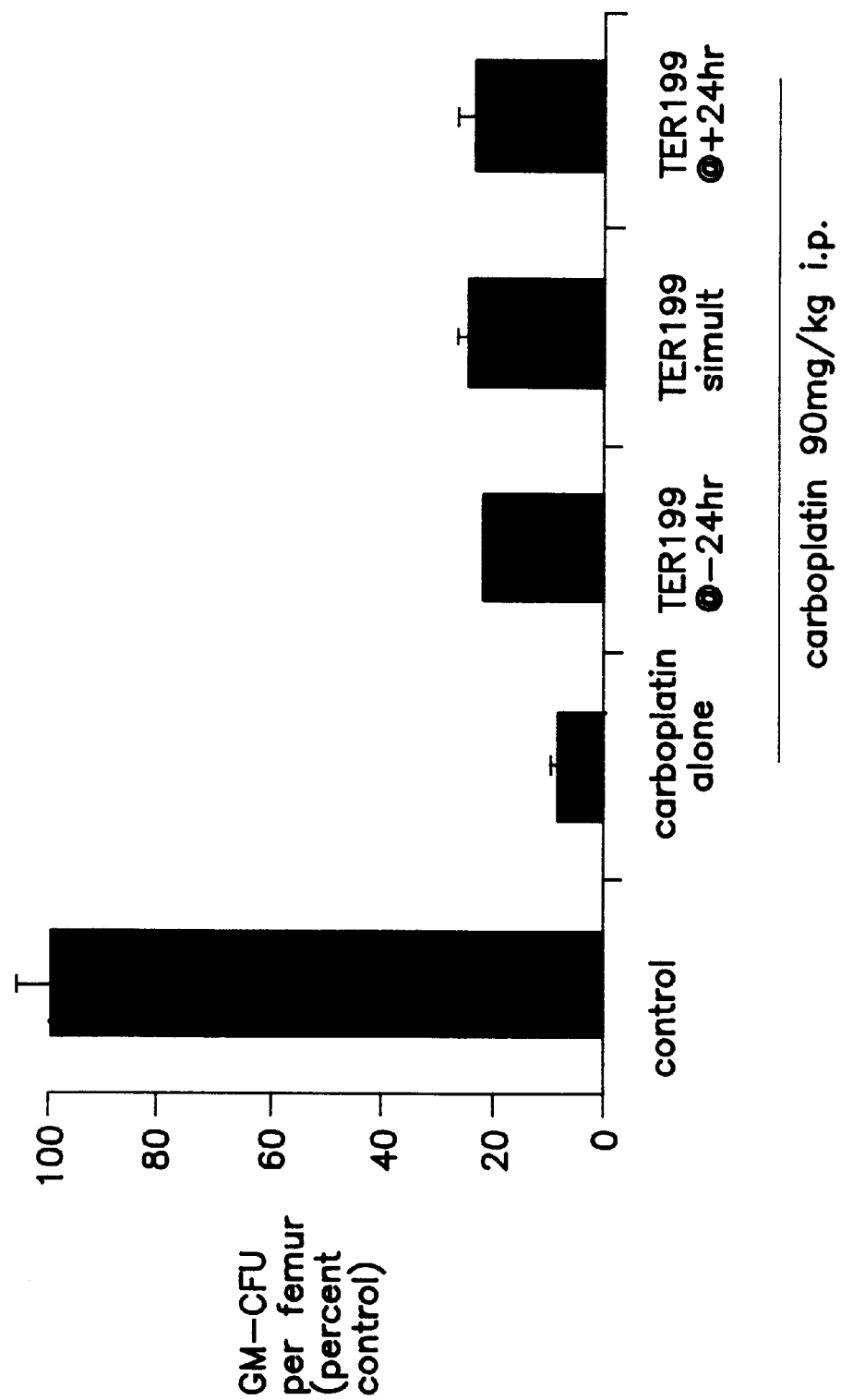
FIGS. 12A and 12B are graphs showing the effect of TER199 on carboplatin-induced GM-CFU suppression in mice.
Figure 12B:
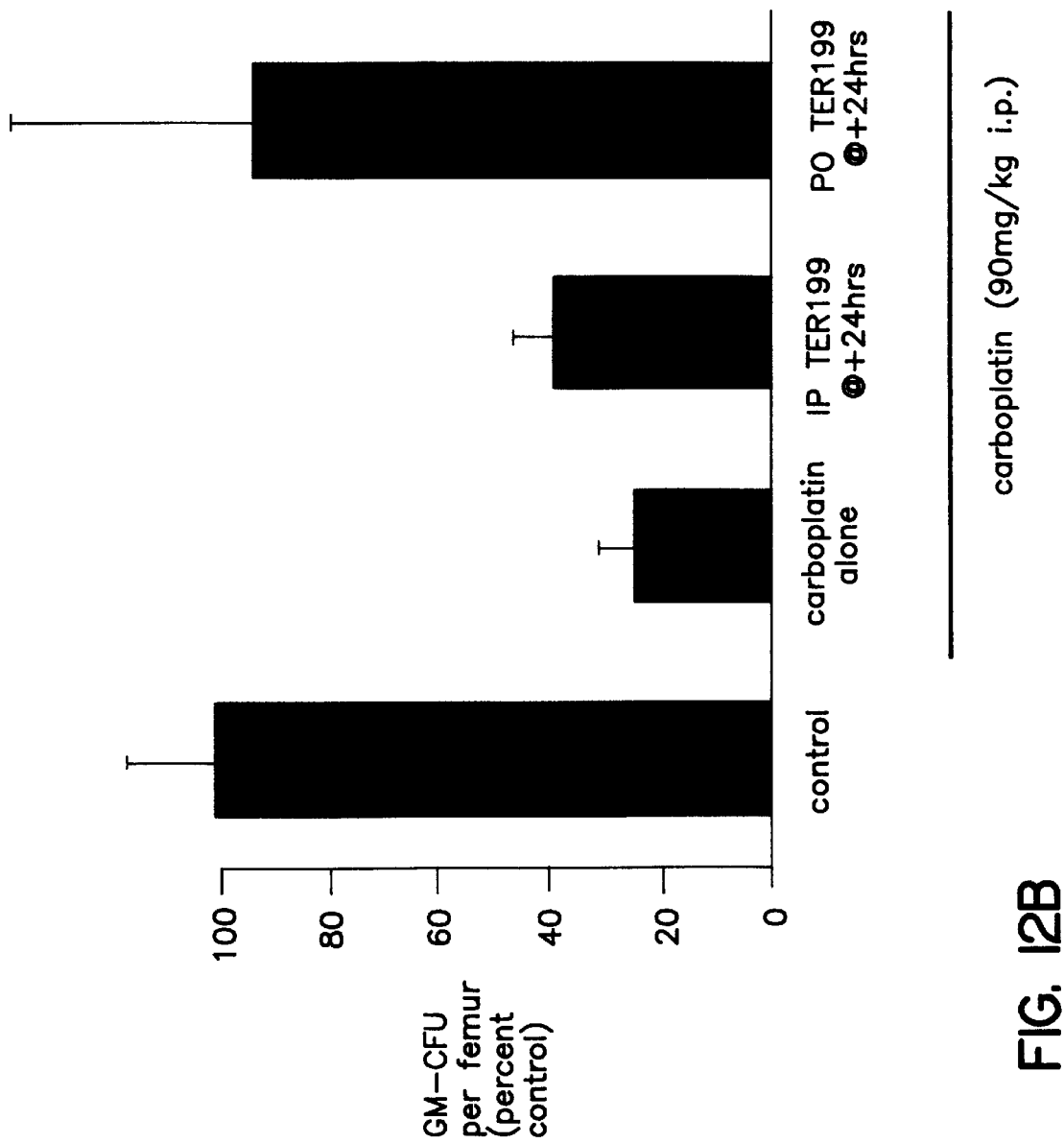

The effect of TER199 on reducing carboplatin-induced GM-CFU supression was determined in experiments similar to those described above. TER199 (120 mg/kg, i.p.) was administered 24 hours before, 24 hours after or simultaneously with carboplatin (90 mg/kg, i.p.). Bone marrows were harvested 24 hours after administration of the second drug. FIG. 12, panel A shows that TER199 reduces carboplatin-induced GM-CFU suppression in mice. Values shown are the mean ± SE of three mice per point. FIG. 12, panel B shows that oral administration of TER199 (150 mg/kg p.o.) is even more effective.

e) Effect of TER199 on cyclophosphamide-induced GM-CFU suppression in mice.

Figure 13A:
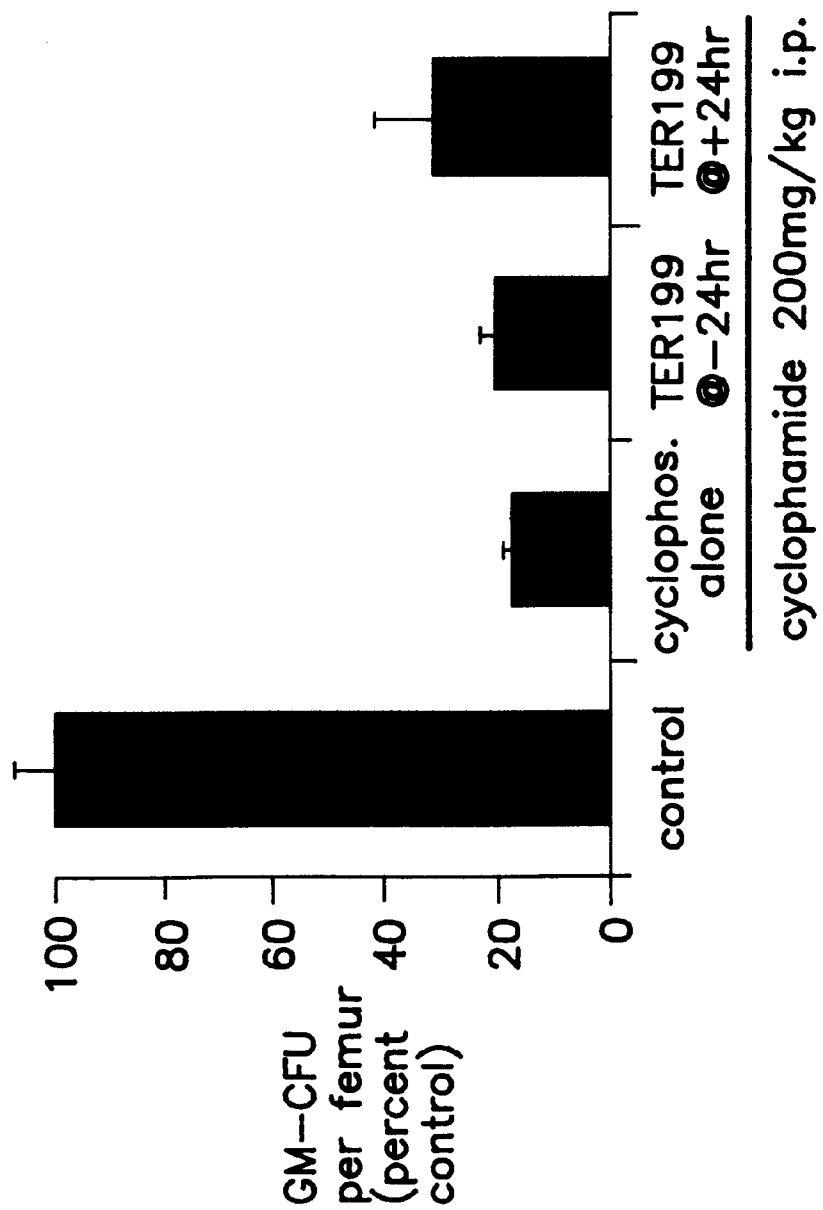
Figure 13B:
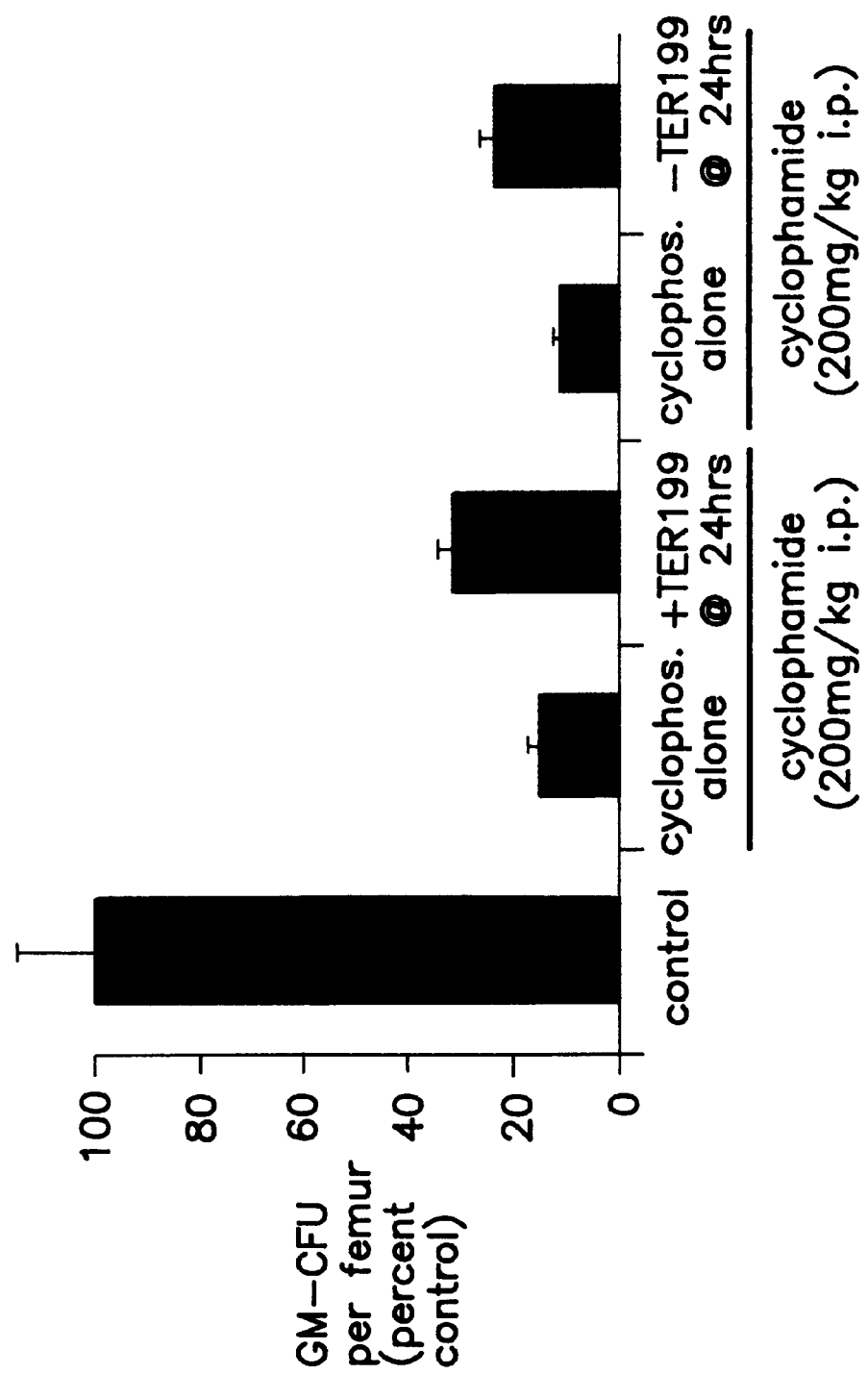

FIG. 13, panel A shows that administration of TER199 (120 mg/kg, i.p.) 24 hours after cyclophosphamide (200 mg/kg, i.p.) reduces GM-CFU suppression in mice. Oral administration of TER199 (150 mg/kg, p.o.) is similarly effective (see FIG. 13, panel B). Values shown are the mean ± SE of three mice per point.

f) Effect of TER199 on mephalan-induced GM-CFU suppression in mice.

The effect of TER199 on reducing melphalan-induced GM-CFU supression was determined in experiments similar to those described above. Injection with melphalan (10 mg/kg i.p.) alone results in only 2% of GM-CFU remaining. The addition of TER199 (90 mg/kg i.p.) given 1 hour prior to melphalan increases the GM-CFU fourfold to 8% of control value (data not shown).

EXAMPLE 11

Peripheral Blood Response to 5-FU Treatment ± TER199 a) 5-FU Treatment ± i.p. administration of TER199.

Figure 14A:
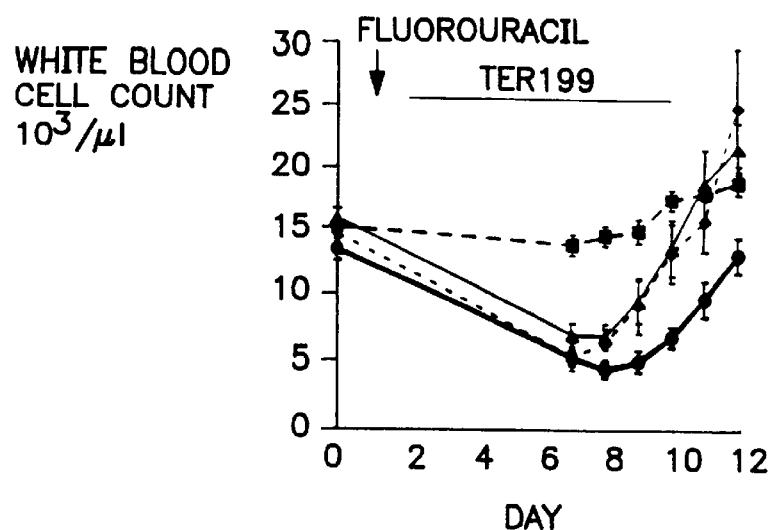
FIG. 14A shows the relationship between time (days) and white blood cell counts in rats following treatment with 5-FU.
Figure 14B:
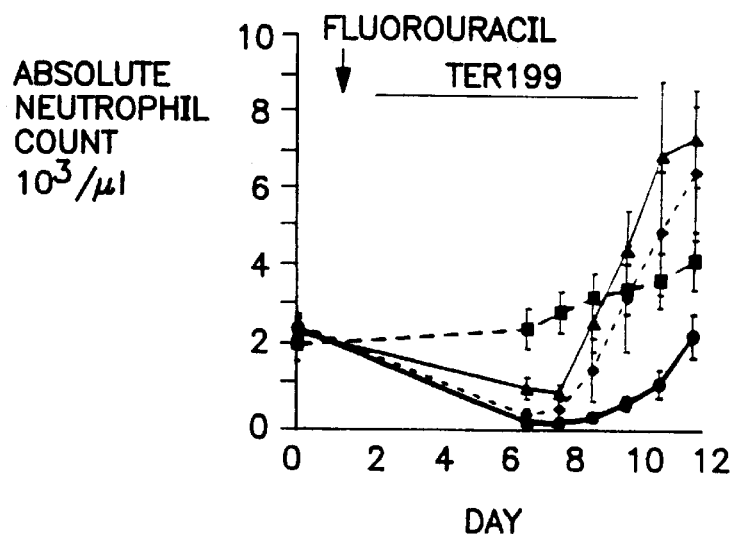
FIG. 14B shows the relationship between time (days) and absolute neutrophil counts in rats following treatment with 5-FU.
Figure 14C:
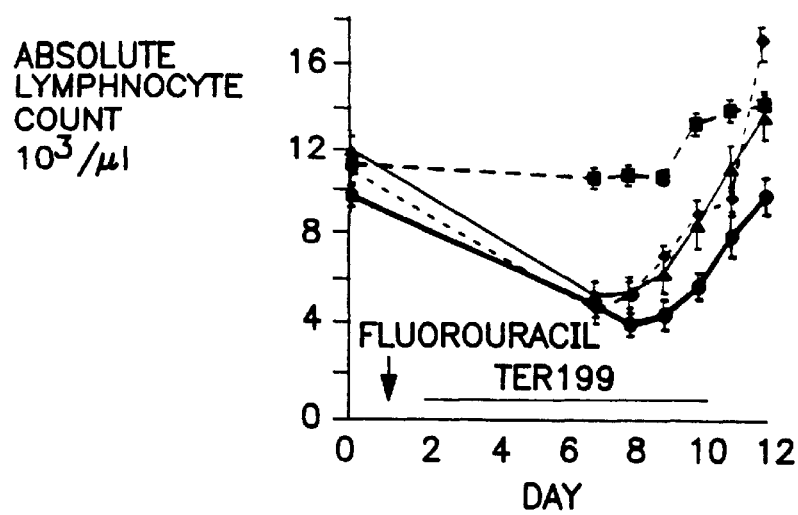
FIG. 14C shows the relationship between time (days) and absolute lymphnocyte counts in rats following treatment with 5-FU.
Figure 14D:
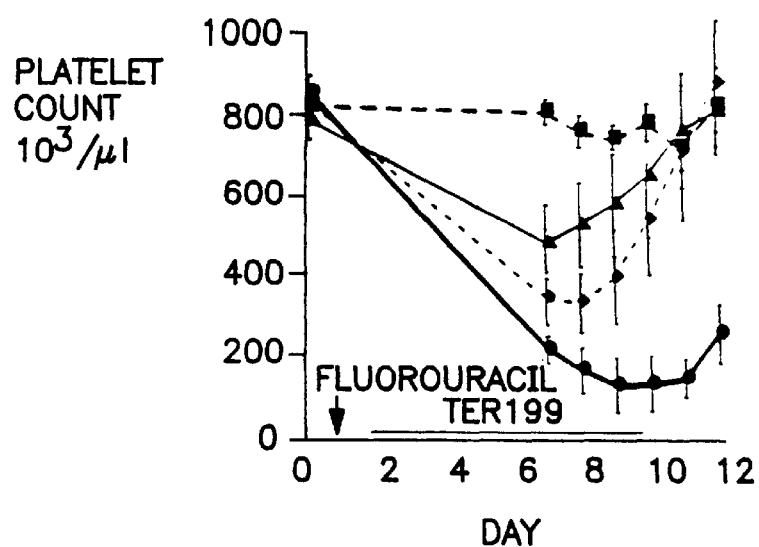
FIG. 14D shows the relationship between time (days) and platelet counts in rats following treatment with 5-FU.
Figure 14E:
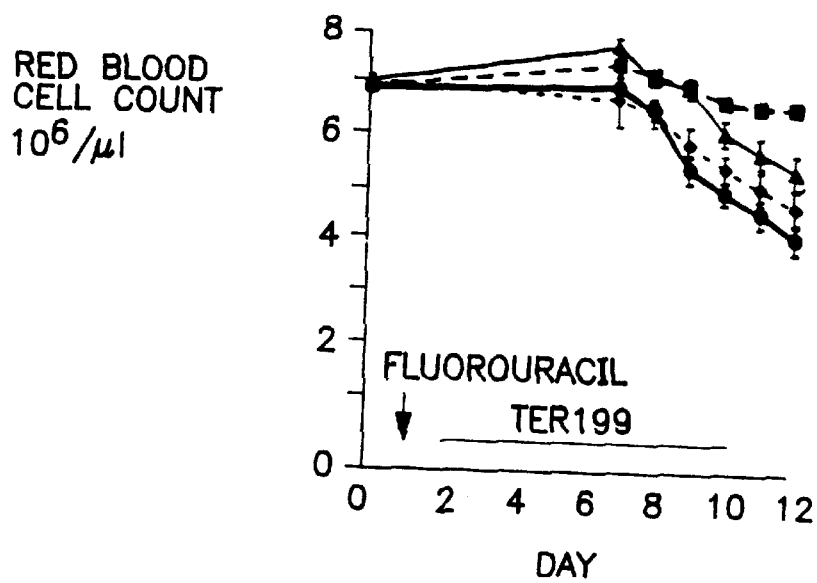
FIG. 14E shows the relationship between time (days) and red blood cell counts in rats following treatment with 5-FU.

The effect of TER199 was evaluated for its ability to lessen the degree and shorten the duration of hematological suppression caused by 5-FU. Sprague-Dawley derived rats were treated according to the schedule below (Table 11). The results of this study are presented in FIGS. 14A and 14B.

TABLE 11

TER199 Peripheral Blood Effects Treatment Schedule

| Group | n= | Day One Injection | Day 2–10 Injection |
|---|---|---|---|
| I | 12 | sterile water | sterile water |
| II | 12 | fluorouracil (150 mg/kg i.p.) | sterile water |
| III | 12 | fluorouracil (150 mg/kg i.p.) | TER199 (60 mg/kg b.i.d. i.p.) |
| IV | 12 | fluorouracil (150 mg/kg i.p.) | TER199 (120 mg/kg q.d. i.p.) |

The response in white blood cell, neutrophil, and lymphocyte levels in the TER199-treated groups reached pretest levels sooner than the 5-FU-treated group and at Day 12 exceeded pretest levels. The pattern differences in this response for each of these cell populations for the TER199-treated groups were significantly different from the 5-FU-treated control group ($p<0.05$). These data demonstrate that, in rats, population levels of white blood cells, neutrophils, and lymphocytes in the peripheral blood supply suppressed by 5-FU, recovered and reached pretest levels more quickly following treatment with TER199 in comparison to placebo-treated animals.

In TER199-treated animals, platelet levels recovered to normal levels by study Day 12. In contrast, the 5-FU control animals platelet levels remained severely suppressed. This response for platelets in the TER199-treated groups was significantly different from the 5-FU-treated control group ($p<0.05$).

Red blood cell counts continually decreased in all groups during the course of this study. Although the observed decrease is reduced in TER199-treated animals compared to the 5-FU control animals, the study was terminated too early to determine if the reduced decline is a delay or an actual reduction in the nadir.

b) 5-FU treatment ± oral administration of TER199.

Figure 15A:
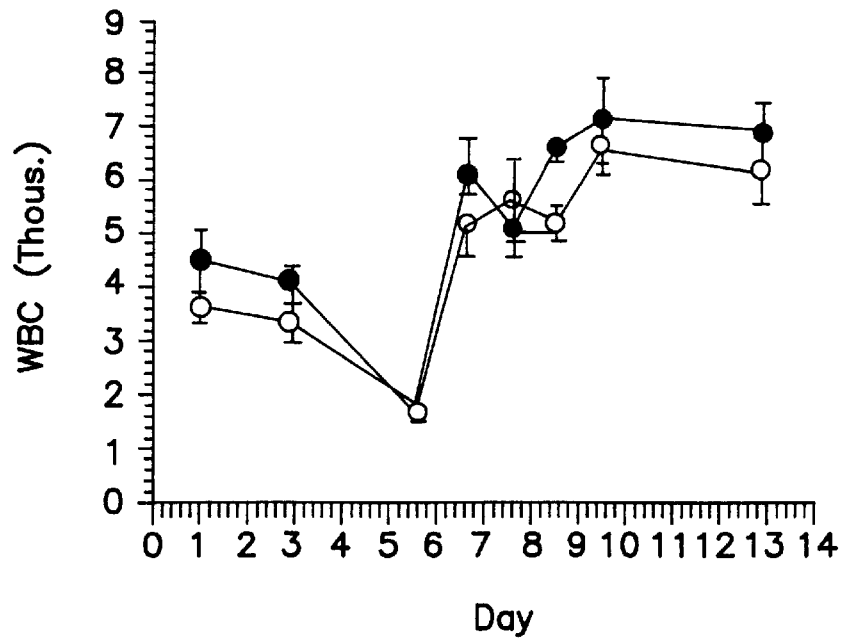
FIG. 15A shows the effect on white blood cell counts after administering 5-FU alone or 5-FU+TER199.
Figure 15B:
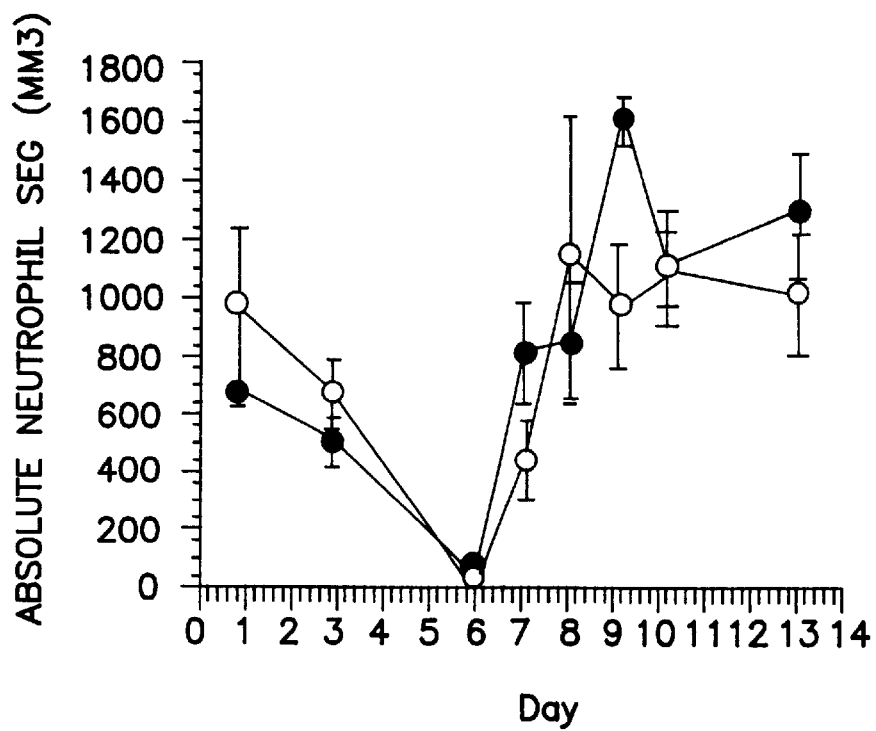
FIG. 15B shows the effect on absolute neutrophil after administering 5-FU alone or 5-FU+TER199.
Figure 15C:
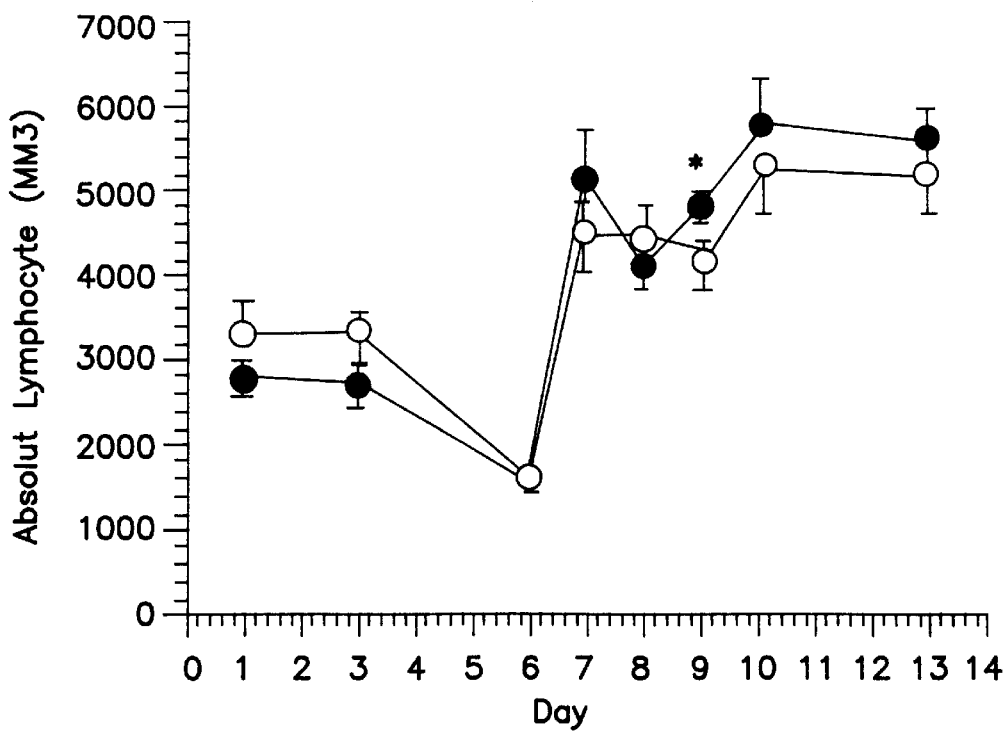
FIG. 15C shows the effect on absolute lymphocyte levels after administering 5-FU alone or 5-FU+TER199.
Figure 15D:
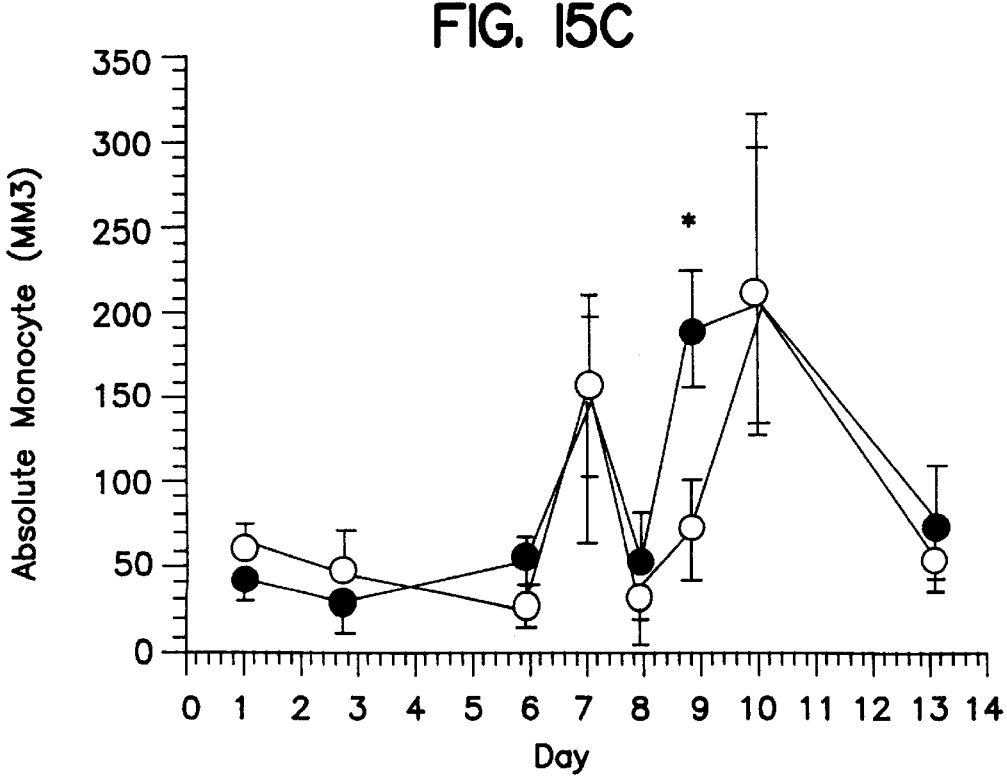
FIG. 15D shows the effect on absolute monocyte levels after administering 5-FU alone or 5-FU+TER199.

The treatment protocol of administering 150 mg/kg 5-FU IP followed 24 hours later by an oral dose of 150 mg/kg TER199 or vehicle in controls, followed 48 hours after 5-FU administration was repeated with additional groups of six mice each. The mice were bled through the retroorbital plexus and the blood samples were analyzed for changes in blood counts. The results in FIGS. 15a–15d show the blood counts of various types of cells for administering 5-FU alone (open circles, ○) or 5-FU plus TER199 (solid circles, ●). FIG. 15a shows the results for total white cell counts; essentially no significant difference was found. FIG. 15b shows the results for neutrophils; a statistically significant difference was obtained only on day 9. FIG. 15c shows the results for lymphocytes; no differences were found. FIG. 15d shows the results for monocytes; there was a statistically significant difference only on day 9.

EXAMPLE 12

Stimulation of Cytokine Production

Human stromal cell cultures were established from freshly obtained human bone marrow as described by East, C. J. et al., *Blood* 5:1172 (1992). On day 2, the cells were exposed for one hour to 100 $\mu$M TER199; culture medium was removed and replaced with fresh medium, and at 24 and 48 hours later, culture supernatants were collected and tested for the presence of interleukin-1 (IL-1). The results are shown in Table 12. IL-1 levels were more than twice those of controls at both 24 and 48 hour time points.

TABLE 12

IL-1 levels in human bone marrow stromal cells in response to TER199

| | IL-1 concentration (% control) | |
|---|---|---|
| Treatment | 24 Hours | 48 Hours |
| None | 114 pg/ml (100) | 97 pg/ml (100) |
| TER199 (100 $\mu$M) | 323 pg/ml (283) | 245 pg/ml (253) |

EXAMPLE 13

Figure 16A:
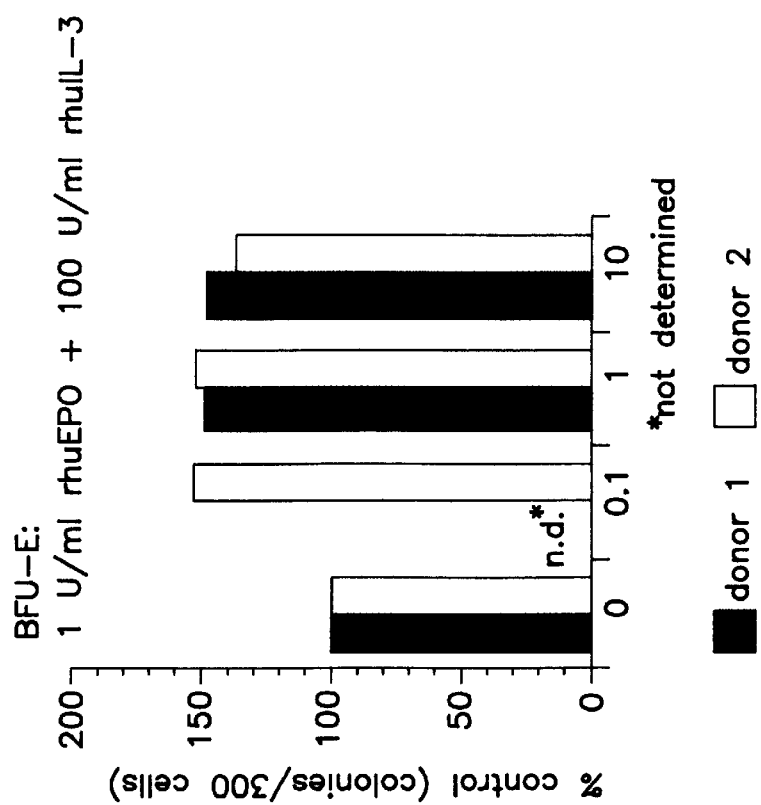
FIGS. 16A and 16B are graphs showing that TER199 enhances cytokine effects in the generation of different progenitors from human cord blood $CD34^{+++}$ cells
Figure 16B:
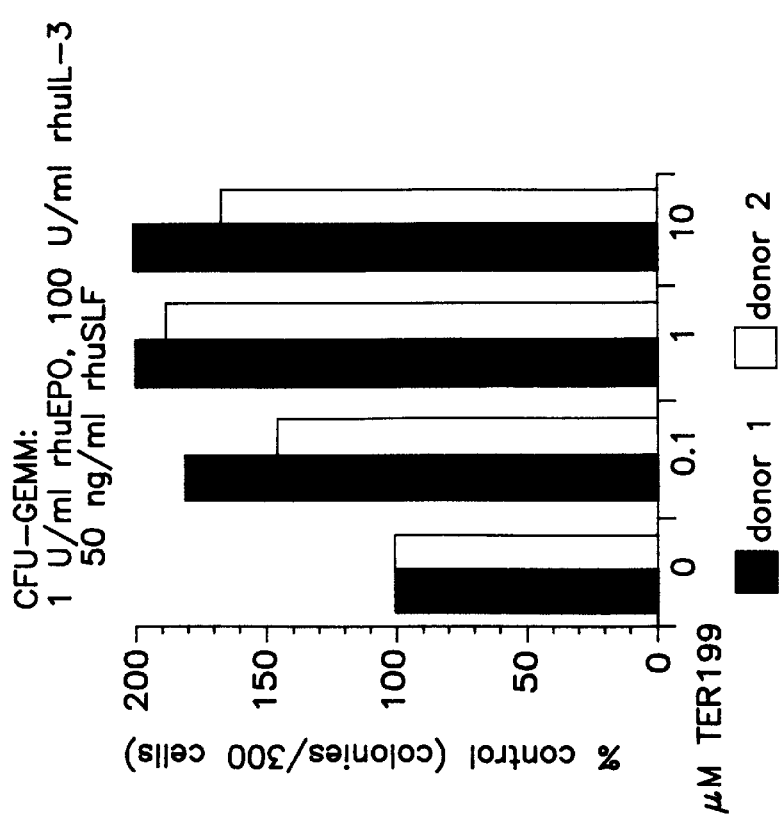

Effect of TER199 on CD34[+++] Differentiation in the Presence of Various Cytokines Highly purified CD34[+++] cells from human cord blood or bone marrow plated at 300 cells/ml were treated with various concentrations of TER199 in the presence of various cytokines. FIG. 16A shows the effect of concentrations of 0.1 μM–10 μM TER199 on granulocyte-erythrocyte-macrophage-megakaryocyte colony formation (CFU-GEMM) in the presence of 1 unit/ml of recombinant erythropoietin, 100 unit/ml of recombinant IL-3, and 50 ng/ml of recombinant steel factor. FIG. 16B also shows the effect of these concentrations of TER199 on erythrocyte progenitor cells (BFU-E) in the presence of 1 unit/ml recombinant erythropoietin and 100 unit/ml of recombinant IL-3. As shown, these concentrations have modest positive effects on both CFU-GEMM and BFU-E at even the lowest concentration (0.1 μM) of TER199. These results appear consistent as regards two individual donors.

EXAMPLE 14

Preferred Method for Synthesis of TER199

Figure 17A:
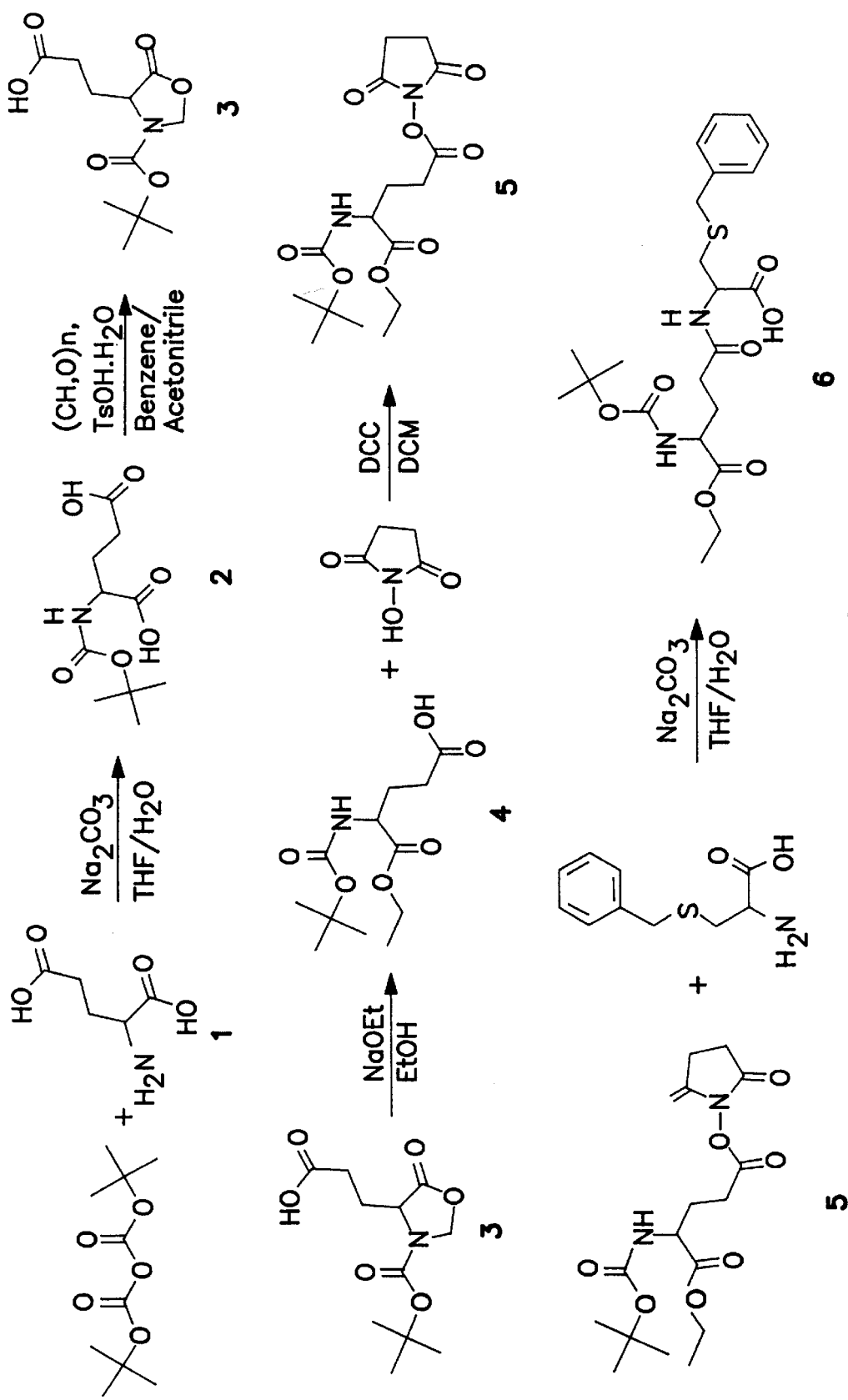
FIG. 17A shows several steps of a preferred method for synthesis of TER199.
Figure 17B:
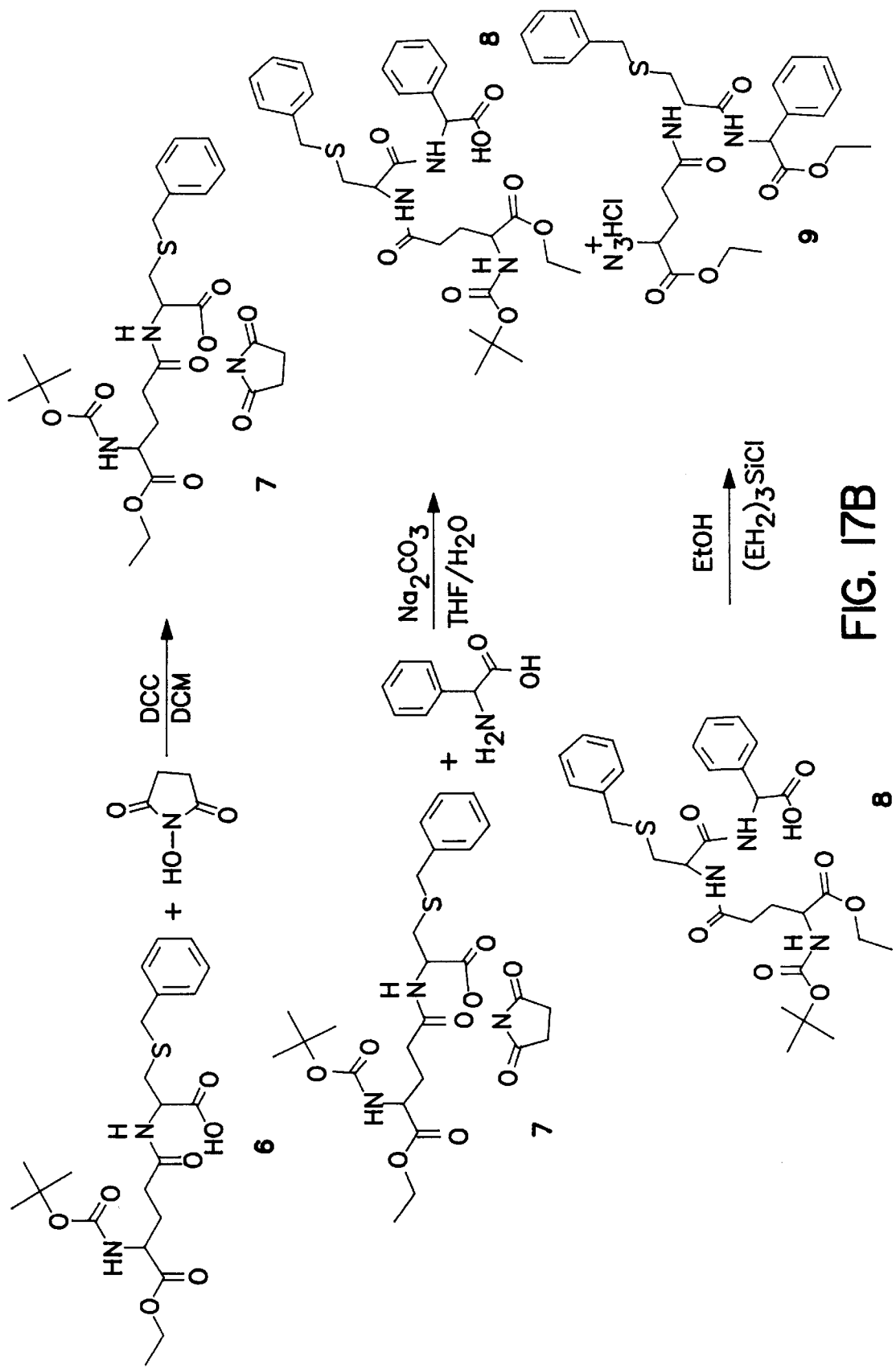
FIG. 17B shows a continuation of the steps of FIG. 17A for a preferred method for synthesis of TER199.

The overall scheme for synthesis of TER199 is shown in FIGS. 17A and 17B.

TER199 is a fluffy white powder with a melting point of 145–150° C. having the native L configuration for both the cysteine and γ-glutamyl residues and the D form of phenylglycine. When synthesized by the method shown in FIG. 17, the product obtained is analyzed using standard techniques to confirm its identity.

We claim:

1. A method to stimulate hematopoiesis, protect hematopoietic cells from damage caused by radiation or chemotherapy, or potentiate the stimulatory action of one or a combination of cytokines on colony formation by hematopoietic progenitor cells, which method comprises contacting bone marrow or peripheral blood or fractions thereof with a compound of the formula

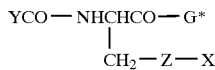

or the ester, amide, ester/amide or salt forms thereof, wherein

YCO is γ-glu or β-asp;

G* is phenylglycine or glycine;

Z is CH$_2$, O or S; and

X is a hydrocarbon radical selected from the group consisting of C6–C8 alkyl, benzyl, naphthyl, substituted benzyl and substituted naphthyl, in an amount and for a time effective to stimulate hematopoiesis, protect said hematopoietic cells from said damage, or potentiate said stimulatory action of said cytokine or cytokines, in said bone marrow, peripheral blood, or fraction.

2. The method of claim 1 wherein Z is S.

3. The method of claim 1 wherein X is hexyl, heptyl, octyl, benzyl or naphthyl.

4. The method of claim 3 wherein X is benzyl or octyl.

5. The method of claim 1 wherein the compound is in the diester form.

6. The method of claim 1 wherein the compound is a diester of γ-glu-C(Bz)-G, of γ-glu-C(octyl)-G, of γ-glu-C(Bz)-φG, or of γ-glu-C(octyl)-φG.

7. The method of claim 1 wherein the compound is a diester of γ-glu-C(Bz)-φG or γ-glu-C(octyl)-G.

8. The method of claim 7 wherein the compound of is a diethyl ester of γ-glu-C(Bz)-φG.

9. The method of claim 8 wherein the γ-glu and C(Bz) residues are in the native L configuration and the φG residue is in the D configuration.

10. The method of claim 1 wherein said contacting is effected by administering said compound or a pharmaceutical composition thereof to a subject in need of said stimulating, protecting or potentiation, in an amount effective to stimulate said hematopoiesis, protect said hematopoietic cells from said damage, or potentiate said action of said cytokines.

11. The method of claim 10 wherein said subject is a human.

12. The method of claim 10 wherein said administering is intraperitoneal, intravenous or oral.

13. A method to protect a subject from the destructive effects of a chemotherapeutic agent or irradiation, which method comprises administering a compound of the formula

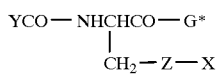

or the ester, amide, ester/amide or salt forms thereof, wherein YCO is γ-glu or β-asp;

G* is phenylglycine or glycine;

Z is CH$_2$, O or S; and

X is a hydrocarbon radical selected from the group consisting of C6–C8 alkyl, benzyl, naphthyl, substituted benzyl and substituted naphthyl, to said subject in an amount and for a time effective to exert said protective effects.

14. The method of claim 13 wherein Z is S.

15. The method of claim 13 wherein X is hexyl, heptyl, octyl, benzyl or naphthyl.

16. The method of claim 15 wherein X is benzyl or octyl.

17. The method of claim 13 wherein the compound is in the diester form.

18. The method of claim 13 wherein the compound is a diester of γ-glu-C(Bz)-G, of γ-glu-C(octyl)-G, of γ-glu-C(Bz)-φG, or of γ-glu-C(octyl)-φG.

19. The method of claim 13 wherein the compound is a diester of γ-glu-C(Bz)-φG or γ-glu-C(octyl)-G.

20. The method of claim 13 wherein the compound of is a diethyl ester of γ-glu-C(Bz)-φG.

21. The method of claim 20 wherein the γ-glu and C(Bz) residues are in the native L configuration and the φG residue is in the D configuration.

22. The method of claim 13 wherein said subject is a human.

23. The method of claim 13 wherein said administering is intraperitoneal, intravenous or oral.

24. A method to potentiate the effect of a chemotherapeutic agent administered to a subject, which method comprises administering a compound of the formula

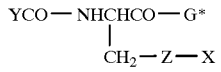

or the ester, amide, ester/amide or salt forms thereof, wherein YCO is γ-glu or β-asp;

G* is phenylglycine or glycine;

Z is CH$_2$, O or S; and

X is a hydrocarbon radical selected from the group consisting of C6–C8 alkyl, benzyl, naphthyl, substituted benzyl and substituted naphthyl, to said subject in an amount and for a time effective to potentiate said effect.

25. The method of claim 24 wherein Z is S.

26. The method of claim 24 wherein X is hexyl, heptyl, octyl, benzyl or naphthyl.

27. The method of claim 26 wherein X is benzyl or octyl.

28. The method of claim 24 wherein the compound is in the diester form.

29. The method of claim 24 wherein the compound is a diester of γ-glu-C(Bz)-G, of γ-glu-C(octyl)-G, of γ-glu-C(Bz)-φG, or of γ-glu-C(octyl)-φG.

30. The method of claim 24 wherein the compound is a diester of γ-glu-C(Bz)-φG or γ-glu-C(octyl)-G.

31. The method of claim 30 wherein the compound is a diethyl ester of γ-glu-C(Bz)-φG.

32. The method of claim 31 wherein the γ-glu and C(Bz) residues are in the native L configuraiton and the φG residue is in the D configuration.

33. The method of claim 24 wherein said subject is a human.

34. The method of claim 24 wherein said administering is intraperitoneal or intravenous or oral.

35. A pharmaceutical composition in unit dosage form which contains, as active ingredient, an effective amount of a compound of the formula

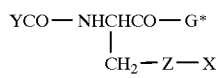

or the ester, amide, ester/amide or salt forms thereof, wherein YCO is γ-glu or β-asp;

G* is phenylglycine or glycine;

Z is $CH_2$, O or S; and

X is a hydrocarbon radical selected from the group consisting of C6–C8 alkyl, benzyl, naphthyl, substituted benzyl and substituted naphthyl, in admixture with a pharmaceutically acceptable excipient.

36. The composition of claim 35 which is suitable for oral administration.

37. The composition of claim 36 which is in the form of a tablet, pill, capsule, syrup, powder or tonic.

38. The method of claim 1, wherein said compound inhibits the π subclass of glutathione S-transferase isoenzyme.

* * * * *